(12) United States Patent
Funke

(10) Patent No.: US 7,082,328 B2
(45) Date of Patent: Jul. 25, 2006

(54) METHODS AND APPARATUS FOR CONTROLLING A PACING SYSTEM IN THE PRESENCE OF EMI

(75) Inventor: Hermann D. Funke, Gemmenich (BE)

(73) Assignee: Medtronic, Inc., Minneapolis, MN (US)

( * ) Notice: Subject to any disclaimer, the term of this patent is extended or adjusted under 35 U.S.C. 154(b) by 657 days.

(21) Appl. No.: 10/143,392

(22) Filed: May 10, 2002

(65) Prior Publication Data

US 2003/0144705 A1 Jul. 31, 2003

Related U.S. Application Data

(63) Continuation-in-part of application No. 10/059,586, filed on Jan. 29, 2002.

(51) Int. Cl.
*A61N 1/362* (2006.01)
(52) U.S. Cl. .......................................................... 607/9
(58) Field of Classification Search .................. 607/9
See application file for complete search history.

(56) References Cited

U.S. PATENT DOCUMENTS

| | | | |
|---|---|---|---|
| 3,688,776 A | 9/1972 | Kenny | |
| 4,301,804 A | 11/1981 | Thompson et al. ... | 128/419 PG |
| 4,386,610 A * | 6/1983 | Leckrone ........................ | 607/9 |
| 4,541,431 A | 9/1985 | Ibrahim | |
| 4,941,471 A | 7/1990 | Mehra ................... | 128/419 PG |
| 5,170,806 A | 12/1992 | Colen .......................... | 128/901 |
| 5,197,468 A | 3/1993 | Proctor et al. ......... | 128/419 PG |
| 5,217,010 A | 6/1993 | Tsitlik et al. .......... | 128/419 PG |
| 5,438,990 A | 8/1995 | Wahlstrand ............... | 128/653.1 |
| 5,545,185 A | 8/1996 | Denker ......................... | 607/14 |
| 5,629,622 A | 5/1997 | Scampini .................... | 324/247 |
| 5,649,965 A | 7/1997 | Pons et al. ....................... | 607/2 |
| 5,662,694 A | 9/1997 | Lidman et al. ................ | 607/60 |
| 5,697,958 A * | 12/1997 | Paul et al. ..................... | 607/31 |
| 5,722,998 A | 3/1998 | Prutchi et al. ................ | 607/30 |
| 5,814,085 A | 9/1998 | Hill .............................. | 607/14 |
| 5,817,136 A | 10/1998 | Nappholz et al. ............. | 607/17 |
| 6,101,417 A | 8/2000 | Vogel et al. ................... | 607/30 |
| 6,188,926 B1 * | 2/2001 | Vock .............................. | 607/9 |

FOREIGN PATENT DOCUMENTS

| | | |
|---|---|---|
| EP | 0713714 A2 | 5/1996 |
| EP | 0931566 A2 | 7/1999 |
| EP | 0670170 B1 | 5/2002 |

OTHER PUBLICATIONS

Sergio L. Pinski MD et al., "Interference With Cardiac Pacing," (Cardiology Clinics, vol. 18, No. 1 Feb. 2000, pp. 219-239).

Joseph Fetter et al., "The Effects of Nuclear Magnetic Resonance Imagers on External and Implantable Pulse Generators" (PACE, vol. 7, pp. 720-727, Jul.-Aug. 1984.).

\* cited by examiner

*Primary Examiner*—George R. Evanisko
(74) *Attorney, Agent, or Firm*—Paul H. McDowall; Michael C. Soldner; Girma Wolde-Michael

(57) ABSTRACT

Pacing systems are disclosed including detectors for detecting the presence of electromagnetic interference and setting an interference state pacing mode and pacing rate. The interference state pacing mode and pacing rate are altered as a function of patient pacemaker dependency and the prevailing mean heart rate. When pacemaker dependency exists, the pacing rate is maintained and even increased from the prevailing mean heart for the duration of the interference state. When the patient is determined to not be pacemaker dependent, pacing is inhibited or suspended for the duration of the interference state.

6 Claims, 11 Drawing Sheets

METHODS AND APPARATUS FOR CONTROLLING A PACING SYSTEM IN THE PRESENCE OF EMI

CROSS-REFERENCE TO RELATED APPLICATION

This application is a continuation-in-part of U.S. patent application Ser. No. 10/059,586 filed Jan. 29, 2002 for METHOD AND APPARATUS FOR CONTROLLING AN IMPLANTABLE MEDICAL DEVICE IN RESPONSE TO THE PRESENCE OF A MAGNETIC FIELD AND/OR HIGH FREQUENCY RADIATION INTERFERENCE SIGNALS (P-8110.00) in the name of Hermann D. Funke.

FIELD OF THE INVENTION

This invention relates generally to implantable medical devices and, more particularly, to a method and apparatus for controlling a pacemaker in response to the presence of a relatively strong magnetic field produced by magnetic resonance imaging (MRI) signals and/or high frequency radiation interference signals and other forms of electromagnetic interference (EMI) comprising an interference state.

DESCRIPTION OF THE RELATED ART

Considerable advances have been made in the fields of electronics and medicine since the introduction of implantable pacemakers in the 1960s. Currently available implantable medical devices (IMDs) include pacemakers, implantable cardioverters/defibrillators (ICDs), neural stimulators, and drug administering devices, among others. State of the art IMDs are vastly more sophisticated and complex than earlier ones and are capable of performing significantly more complex tasks. Additionally, the therapeutic benefits of such IMDs have been well proven.

Single chamber, dual chamber and bi-ventricular or other multi-chamber pacemakers and ICDs typically include a pacing system (hereafter it shall be understood that such ICDs contain a pacing system) that operates in a pacing mode to deliver pacing pulses when necessary to one or more heart chamber. The pacing modes of such pacing systems are typically programmable and can be changed within a range of possible operating modes by a physician employing a programmer to command a mode change. More complex pacing systems have been devised that automatically change pacing mode under certain circumstances. In addition, rate responsive pacing systems operate in pacing modes and at pacing rates dictated by the patient's need for cardiac output as determined by a wide variety of sensors and rate determining algorithms. Most pacing modes rely upon accurate detection of distinctive features of the atrial and/or ventricular (A/V) electrograms (EGMs), particularly the detection of and distinction between atrial P-waves, ventricular R-waves, and, in certain cases, T-waves of the characteristic PQRST complex, to function properly in a prevailing operating mode.

A pacing mode code devised by the Inter-Society Commission for Heart Disease Resources (ICHD) to characterize the possible pacing modes has been universally adopted in the industry. The ICHD code comprises three letters in three respective left to right positions, the first letter (A for atrial, V, for ventricular, and D for both) indicating the chamber(s) paced, the second letter (A for atrial, V, for ventricular, and D for both) indicating the chamber(s) sensed, and the third letter indicating the mode of response, triggered (T) or inhibited (I). If a rate response function is present, it is indicated in the code by a further parenthetically enclosed letter R. Furthermore, if a function is absent or inhibited, it is indicated by the letter O. The pacing code is used at times to indicate a programmed pacing mode and at other times to indicate a current pacing mode of a pacing system capable of operating in more than one pacing mode. Thus, for example, pacing modes can comprise fixed rate pacing modes AOO, VOO, DOO, inhibited (demand) pacing modes AAI, AAI(R) VVI, VVI(R), DDI, DDI(R), triggered pacing modes AAT, AAT(R), VVT, VVT(R), DDT, DDT(R), the AV sequential mode DVI, DVI(R), the AV synchronous mode VAT, VAT(R), the fully synchronous mode DDD, DDD(R) and certain variations on these modes. The appended "(R)" indicates the rate response function is present but may be operative or inoperative depending upon the relationship of the determined rate response rate to upper and lower rate limits and/or a sensed atrial rate. The appended "R" indicates the rate response function is present and is operative dependent upon a rate control parameter (RCP) signal developed by one or more physiologic sensor. The totally inhibited mode is indicated by pacing mode OOO.

In the DDD pacing mode, atrial and ventricular pacing is inhibited depending upon the occurrence of non-refractory atrial and ventricular sense events during the time-out of a pacing escape interval and an AV delay or delivered at the time-out of the pacing escape interval and an AV delay, respectively, in a manner well known in the art. In the DDDR pacing mode, the pacing escape interval is adjusted between a pacing lower rate, e.g. 60 bpm, and a pacing upper rate limit, e.g., 120 bpm, as a function of the physiologic need for cardiac output in any of the rate response modes known in the art.

The atrial and/or ventricular sense amplifiers of pacemakers and ICDs are coupled through leads to pace/sense electrodes located at sites in or close to the atria and/or ventricles traversed by the features of interest of the A/V EGM. Sense events are generated by the sense amplifiers when the signal levels are within a frequency band and meet sensing threshold criteria. Capacitors and high voltage blocking diodes are incorporated into the circuitry between the sense amplifiers and the lead conductors and the circuitry is shielded to an extent by enclosure within a hermetically sealed conductive housing.

Despite precautions, EMI signals from a wide variety of interference sources can still be superimposed upon the A/V EGM and mistakenly cause the pacemaker and ICD sense amplifiers to generate sense events falsely signifying detection of P-waves, R-waves, and, in certain cases, T-waves. Thus, high rate sense events can be generated by the sense amplifiers during EMI episodes. Very sophisticated noise detection algorithms have been implemented over the years in hardware and firmware associated with the atrial and/or ventricular sense amplifiers and signal processors of atrial and ventricular sensing channels to assess whether or not high rate sense events reflect true P-waves or R-waves or the presence of EMI. Typically, pacing systems change operating mode from the programmed or prevailing operating modes (typically DDD or DDDR and sub-sets thereof in dual chamber pacing and AAI or AAIR, VVI or VVIR in single chamber pacing) to a designated safe "reversion mode" when and as long as EMI criteria are satisfied. The typical reversion mode is fixed rate pacing at the programmed lower rate. The wide variety of EMI sources and their effects on pacemaker and ICD sense amplifiers and resulting pacing operations and modes are described, for example, in the article by Sergio L. Pinski MD et al., entitled "Interference with Cardiac Pacing" (CARDIOLOGY CLINICS, Vol. 18, No. 1February 2000, pp. 219–239).

Most incidences of exposure of patient-implanted pacemakers and ICDs to sources of EMI are inadvertent and unintentional. However, such patients are often subjected intentionally to a variety of EMI sources including EMI emitted by other IMDs implanted in the same patient or external security equipment and medical equipment as reported in the Pinski et al. article. In particular, the frequency of exposure of such patients to nuclear magnetic resonance (NMR) imaging devices during a magnetic resonance imaging (MRI) scanning session is increasing as MRI scanning has proven to be a useful tool in diagnosing disease and injury.

The intense magnetic field emitted during an MRI scanning session (or other intense magnetic fields that the patient may inadvertently encounter) can cause currents to be induced in the conductors of the leads and other circuits or components coupled between the pace/sense electrodes and the sense amplifiers that distort or corrupt the EGM. In addition, high frequency (HF) radiation interference signals produced by radar, mobile phone transmitters, and the like, typically cause the A/V EGM to also become distorted and/or corrupted.

The distortion and corruption of the EGM presented to the sense amplifiers of such IMDs results in undersensing or oversensing P-waves and/or R-waves which can inhibit delivery of pacing or a cardioversion/defibrillation therapy, or inadvertently trigger delivery of high rate pacing or a cardioversion/defibrillation shock or cause pacemakers or ICD pacing systems to revert to a safe reversion mode as described above.

Pacemakers and ICDs have been typically designed to rely upon the use of a magnetic field sensor, e.g., a reed switch, during telemetry sessions or at other times to switch pacing mode from the programmed or prevailing mode to a further "magnet mode", typically the AOO, VOO or DOO pacing mode. One historic but discontinued use of the magnetic field sensor was to induce the fully inhibited OOO pacing mode to allow the physician to inhibit the delivery of pacing pulses so that the underlying cardiac EGM can be exhibited as an ECG tracing for diagnostic purposes. More recently, the fully inhibited OOO pacing mode is only made available as a programmable temporary mode, and the magnet mode is AOO, VOO or DOO pacing mode providing fixed rate, single or dual chamber pacing at a particular magnet mode pacing rate or the programmed lower pacing rate. The unintentional exposure to intense magnetic fields can cause a mode switch from the prevailing pacing mode to the magnet mode. The intentional exposure to the intense magnetic fields emitted by NMR equipment during MRI scanning can also be sensed by the typical magnetic field responsive reed switch or other field sensor and cause the magnet mode switch to take place.

These effects are also described in the article by Joseph Fetter et al. "The Effects of Nuclear Magnetic Resonance Imagers on External and Implantable Pulse Generators" (PACE, Vol. 7, pp. 720–727, July–August 1984).

Thus, in one way or another, the sense amplifiers or sensing circuits cannot accurately sense the underlying heart rate during the MRI scanning session due to the response to the magnetic field and electromagnetic interference signals. The patient's spontaneous heart rate can increase during the MRI scanning session and surpass a prevailing magnet mode pacing rate or reversion mode rate due to the patient's anxiety resulting in potentially harmful "parasystole" when the pacing system attempts to pace the heart at a rate lower than the patient's actual spontaneous heart rate. For example, the delivery of a ventricular pacing pulse during a T-wave of a spontaneous ventricular depolarization can trigger ventricular tachyarrhythmias including lethal ventricular fibrillation. Similarly, the delivery of an atrial pacing pulse at the end of the atrial refractory period following a spontaneous atrial depolarization can trigger atrial tachyarrhythmias including atrial fibrillation. Thus, parasystole is a highly undesirable condition potentially causing serious harm to the patient, including fatality.

Alternatively, the spontaneous heart rate may be considerably slower than the "magnet mode" pacing rate or the reversion pacing rate (whichever is controlling under the influence of the magnetic field or EMI, respectively), and, under magnet mode rate pacing, the heart may be overdriven (overdriven) at a harmful rate. The heart rate increased by this mechanism can cause patients to experience angina, especially when the patient is suffering from coronary disease because higher heart rates shorten the diastolic interval during which the myocardium normally is perfused with blood, and un-physiologically high stimulation rates can drive such patients into myocardial infarction.

In addition, when a patient is entirely pacemaker dependent and the pacing system is operating in the DDD or DDDR pacing mode, the pacing rate varies between a pacing upper rate limit and a pacing lower rate depending upon the physiologic need for cardiac output. The patient may be adversely affected when the pacing rate abruptly switches to the pacing lower rate or an intermediate magnet mode or reversion rate that is lower than the prevailing physiologic pacing rate. A patient could lose consciousness due to a sudden loss of blood pressure and be injured if driving a vehicle or involved in a stressful activity.

The present invention is directed to overcoming, or at least reducing the effects of, one or more of the problems set forth above.

SUMMARY OF THE INVENTION

In one aspect of the present invention, methods and systems that control a pacing system of a pacemaker or ICD implanted in a patient are provided during episodes of electromagnetic interference including both strong magnetic fields or high magnitude radiation signals or electromagnetic fields or electrical signals applied to the patient's body that induce noise signals in circuitry of the IMD all collectively referred to hereafter as EMI unless specifically distinguished. The methods and system operate to detect such EMI, declare (i.e., determine) an interference state if certain conditions are met, and increase the pacing rate from the prevailing pacing rate preceding declaration of an interference state by an increment. The increment can be either a fixed pacing rate increase or a percentage of the prevailing paced or spontaneous mean heart rate (MHR) preceding the onset of the interference. The declaration of the interference state can be explicit or simply a determined condition upon which a subsequent action depends. In this specification the, state and condition "declarations" are merely figurative and do not require an expression of a "declaration" in any actual implementation. The term MHR means either an average or a mean value of two or more sequential spontaneous of paced heart cycles, wherein paced heart cycles can be fixed or vary as a function of an RCP.

In a further aspect of the invention embodied in various ways in various alternative embodiments, the interference state pacing mode and pacing rate are altered as a function of patient pacemaker dependency and the prevailing MHR.

When pacemaker dependency exists, the pacing rate is maintained and even increased from the prevailing MHR for the duration of the interference state. When the patient is determined to not be pacemaker dependent, pacing is inhibited or suspended for the duration of the interference state.

Pacemaker dependency is determined as a pacing dependency percentage, designated P %, derived from the ratio of the number of pacing pulses to the total number of pacing pulses and sense events counted over a running time interval preceding the detection of the EMI state. The MHR can be determined over the same or a different running time interval preceding the detection of the EMI state.

In rate responsive pacing modes, the prevailing pacing rate determined by a pacing escape interval is adjusted between a pacing lower rate and a pacing upper rate limit as a function of the physiologic need for cardiac output as determined by any of the rate response modes employing any of the RCPs known in the art. The prevailing pacing rate governs pacing until the interference criteria are met and an interference state is detected (declared). When the interference state is declared, the P % is compared to fixed or programmable pacemaker dependency thresholds comprising a pacemaker independency threshold and one or more pacemaker dependency threshold. Pacing is inhibited if the patient is declared pacemaker independent and pacing continues in a fixed rate mode at a particular interference state rate dependent upon the results of the comparison and the mean heart rate. The pacing rate is set to exceed the MHR by a first amount when the P % exceeds the pacemaker dependency threshold and by a second amount greater than the first amount when the P % exceeds the pacemaker independency threshold but falls below the pacemaker dependency threshold In dual chamber pacing modes, the intrinsic and paced atrial heart rate typically establishes the MHR. An interference state that is declared from comparison of ventricular sense events to interference detection criteria may or may not be confirmed by comparison of atrial sense events to interference detection criteria. If the interference state cannot be confirmed from examination of atrial sense events, then the dual chamber pacing mode is switched to a first safe dual chamber pacing mode, and pacing continues based on the sensed atrial events. If the interference state is confirmed, then a ventricular pacing dependency percentage (V-P %) derived from delivered ventricular pacing pulse and sense event data is compared to ventricular pacemaker dependent criteria. If the patient is declared pacemaker independent in the ventricles (i.e., ventricular pacing is usually inhibited by sensed ventricular events), the pacing mode is switched to an atrial based pacing mode. If not, then the AV delay interval is set to a short AV delay interval, and an atrial pacing dependency percentage (A-P %) derived from atrial paced and sense event data is compared to atrial pacemaker dependent and atrial pacemaker independent criteria. Atrial and ventricular pacing is inhibited if the patient is declared pacemaker independent and pacing continues in a fixed rate mode at a particular interference state rate dependent upon the results of the comparison and the mean heart rate. The atrial pacing rate is set to exceed the MHR by a first amount when the P % exceeds the pacemaker dependency threshold and by a second amount greater than the first amount when the P % exceeds the pacemaker independency threshold but falls below the pacemaker dependency threshold. The dependency and independency thresholds are preferably programmable values.

Pacing in the interference state mode and at the interference state rate continues until the interference criteria are no longer met. The "interference over" criteria can be the same or different than the interference detection criteria.

The interference criteria employed can comprise any of the sense event rate and timing criteria that are customarily employed to declare EMI interference. Alternatively or additionally, a further form of interference usable at least in the single chamber pacing embodiments comprises detecting the presence of a magnetic field proximate to the implantable medical device characteristic of NMR magnetic fields during MRI scanning.

A still further method and apparatus of the invention for detecting interference includes determining if a high frequency (HF) radiation interference signal proximate to the implantable medical device exceeds a pre-selected HF radiation threshold.

The full range of advantages, and features of this invention are only appreciated by a full reading of this specification and a full understanding of the invention. Therefore, to complete this specification, a detailed description of the invention and the preferred embodiments follow, after a brief description of the drawings, wherein additional advantages and features of the invention are disclosed.

This summary of the invention has been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

The invention may be understood by reference to the following description taken in conjunction with the accompanying drawings, in which the leftmost significant digit(s) in the reference numerals denote(s) the first figure in which the respective reference numerals appear, and in which.

DETAILED DESCRIPTION OF SPECIFIC EMBODIMENTS

Illustrative preferred embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Figure 1:
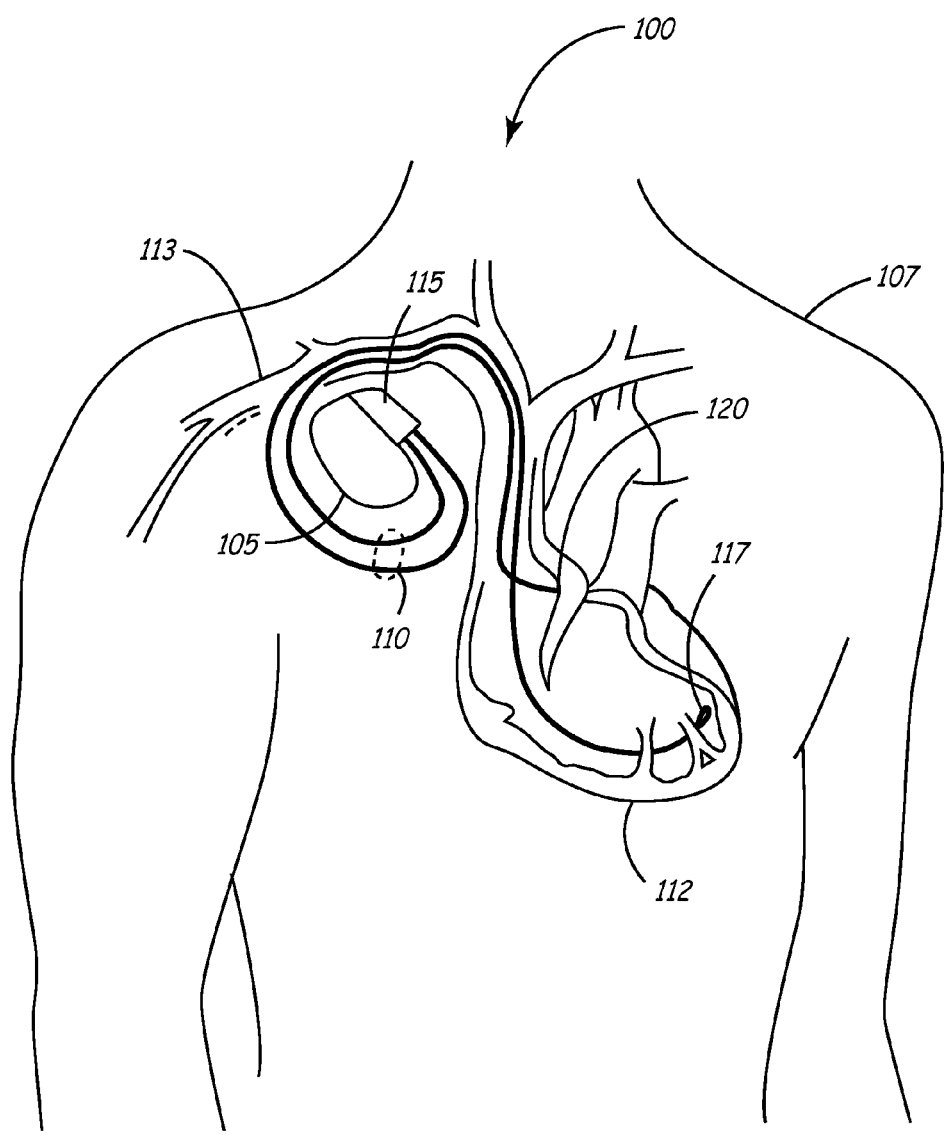
FIG. 1 schematically illustrates one example of a pacing system in which the present invention can be implemented comprising a pacemaker implantable pulse generator and lead(s)

Turning now to the drawings, and specifically referring to FIG. 1, a pacing system 100 is shown in accordance with one embodiment of the present invention. The pacing system 100 includes an implantable pulse generator (IPG) 105 and one or more leads 110 coupled with IPG 105 and implanted in a patient 107. For example, the pacing system 100 takes the form of a pacemaker for regulating the patient's heart rate in response to bradycardias of one or more heart chamber due to a variety of maladies affecting cardiac output. However, it will be understood that the pacing system 100 can be incorporated into an ICD also providing cardioversion/defibrillation therapies in response to the detection of tachyarrhythmias as described above. The various embodiments of the present invention can be incorporated into the functions of single and dual chamber pacing systems 100 embodied in such pacemakers and ICDs without departing from the spirit and scope of the present invention.

The IPG 105 is housed within a hermetically sealed, biologically inert outer housing or container 205, which may itself be conductive so as to serve as an indifferent pace/sense electrode of the pacemaker's pacing/sensing circuit and one or more pacemaker leads, which are collectively identified by reference numeral 110. The leads 110 are electrically coupled to the connector block 115 of the IPG 105 and extend into one or more chamber or cardiac vessel of the patient's heart 112 through a blood vessel 113, such as a vein. One or more exposed conductive pace/sense electrodes for sensing the cardiac EGM and/or delivering electrical pacing stimuli or pulses to the heart 112 are disposed generally near a distal end of the leads 110. The leads 110 may be implanted with their distal ends situated in or adjacent the atrium or the ventricle, or both, of the heart 112.

The pacing system 100 is a dual chamber pacemaker in this illustrated preferred embodiment that may operate in the DDD(R) pacing mode. Consequently, a ventricular lead 116 extends from the IPG 105 into the right ventricle of the heart 112 and at least one distal pace/sense electrode 117 is fixed therein employing an active or passive fixation mechanism of any of the types known in the art. An atrial lead 118 extends from the IPG 105 into the right atrium of the heart 112 and at least one distal pace/sense electrode 120 is fixed therein employing an active or passive fixation mechanism of any of the types known in the art. The pacing system 100 inherently incorporates a single chamber pacemaker and can be programmed to operate as a single or dual chamber pacemaker. The pacing system normally would operate in the DDD(R) pacing mode but can switch between a variety of single and dual chamber pacing modes identified herein including interference state pacing modes under the conditions described herein.

Figure 2:
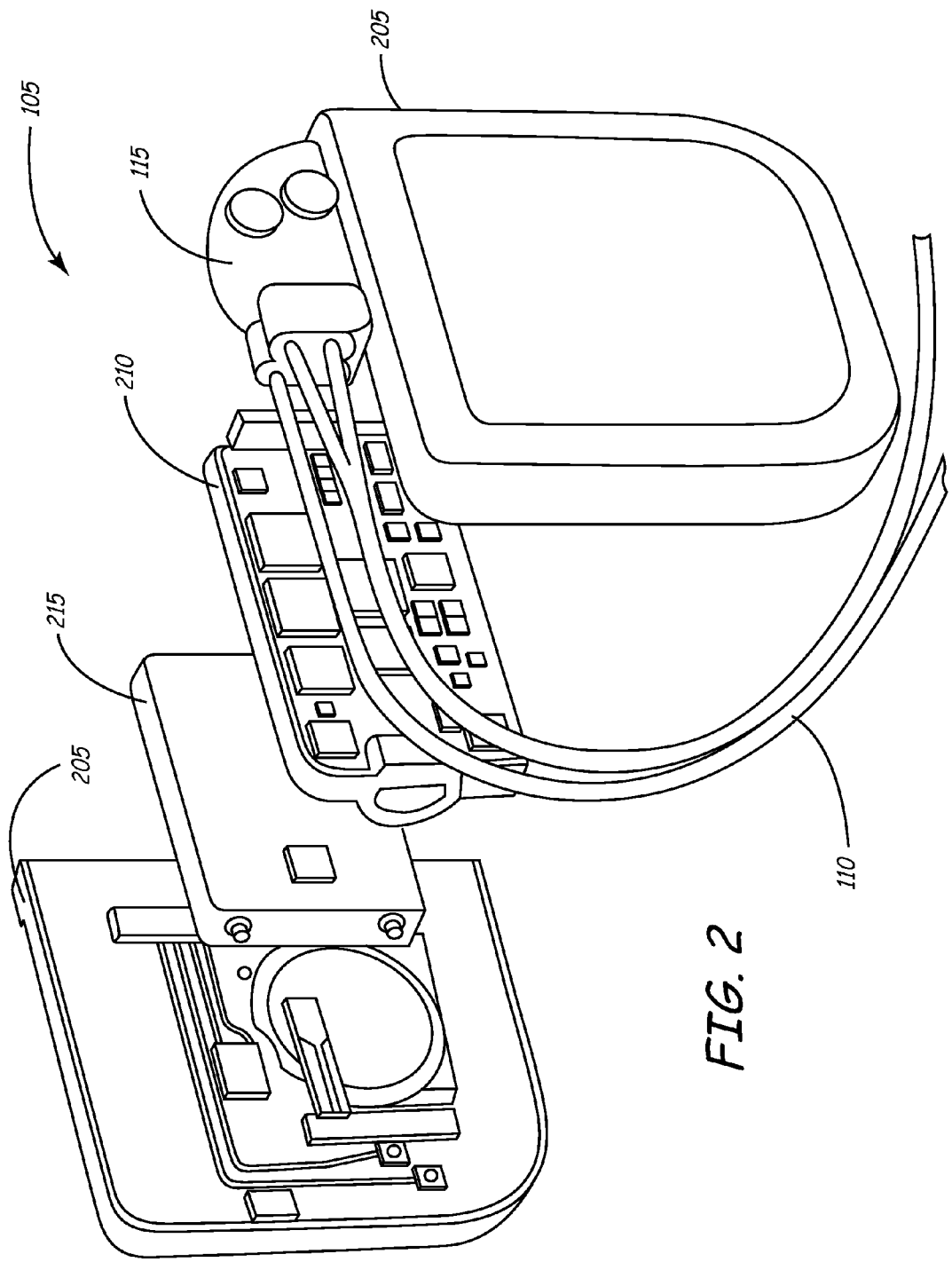
FIG. 2 schematically illustrates a three-dimensional, exploded view of the pacemaker implantable pulse generator of FIG. 1.
Figure 3:
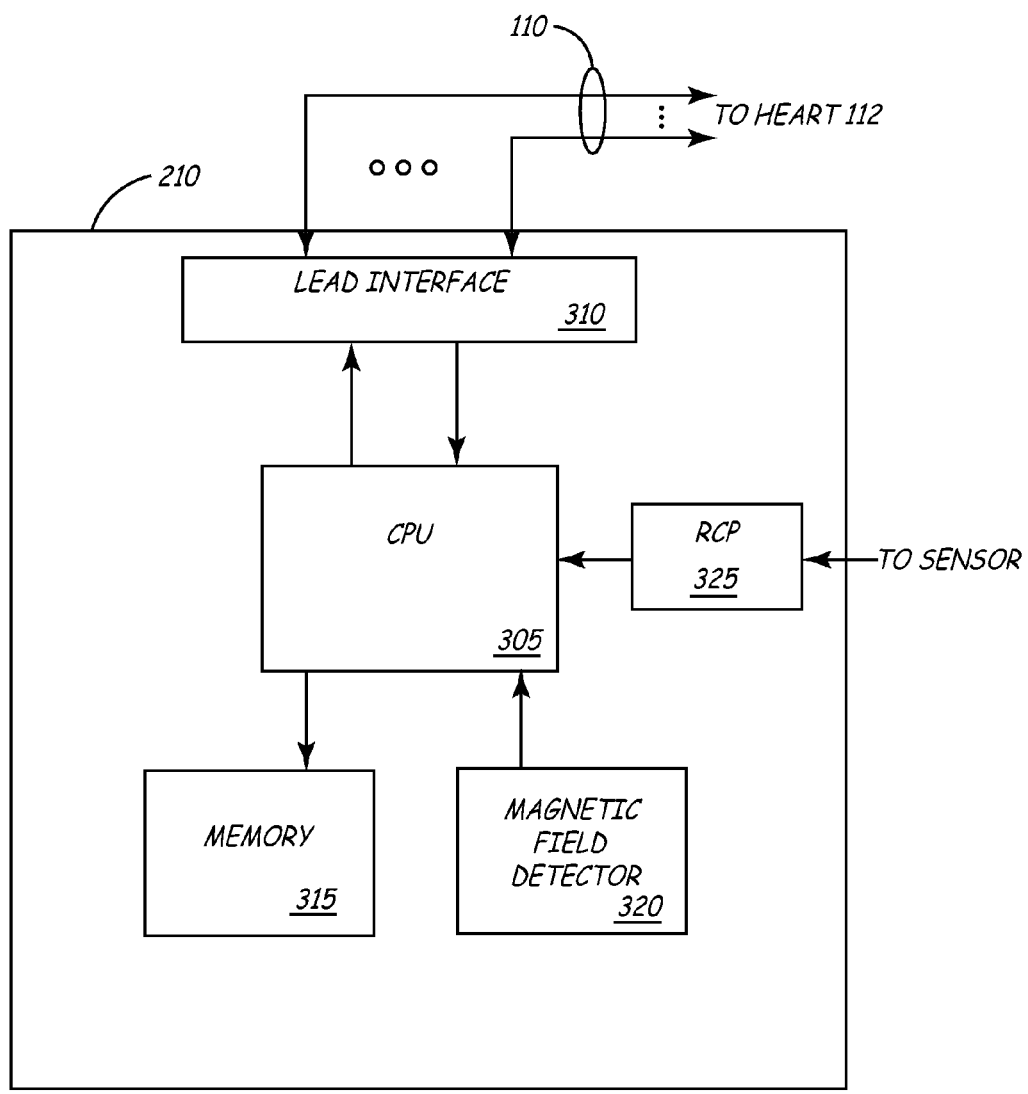
FIG. 3 schematically illustrates a block diagram of a processor unit of the pacing system of FIG. 1 in accordance with one embodiment of the present invention.

In accordance with one embodiment of the present invention, a three-dimensional, exploded view of the IPG 105 is shown in FIG. 2, and a simplified block diagram of the processor unit 210 within the housing 205 of the IPG 105 is shown in FIG. 3. The processor unit 210 and a battery 215 are contained within the hermetically sealed, biologically inert housing 205 to protect them from body fluids within the patient's body 107 in which the device 105 is surgically implanted. It will be appreciated that various other components may be included within the housing 205 of the IPG 105 without departing from the spirit and scope of the present invention.

In one of its most simplistic forms, the processor unit 210 comprises a central processing unit (CPU) 305 for controlling the overall operation of the IPG 105, a lead interface 310 between the leads 110 and the CPU 305, and a RCP circuit 325 responsive to a physiologic sensor (in rate responsive pacing systems) that are all powered by the battery 215. It will be appreciated that the CPU 305 can comprise a micro-computer associated with integrated circuit timers, a state machine, specialized circuits and the like of any of the known types without departing from the spirit and scope of the present invention.

Such single and dual chamber pacing systems have an atrial sensing channel including an atrial sense amplifier within the lead interface 310 that generates an atrial sense event upon detection of a predetermined characteristic of the atrial EGM traversing the atrial pace/sense electrode(s) 120 and/or a ventricular sensing channel including a ventricular sense amplifier that generates a ventricular sense event upon detection of a predetermined characteristic of the ventricular EGM traversing the ventricular pace/sense electrode(s) 117. The lead interface 310 also includes an atrial pacing pulse generator for delivering atrial pacing pulses to the atria through the atrial pace/sense electrode(s) 120 and/or a ventricular pacing pulse generator for delivering ventricular pacing pulses to the ventricles through the ventricular pace/sense electrode(s) 117.

The CPU 305 processes atrial and/or ventricular sense event signals and triggers the delivery of atrial and/or ventricular pacing pulses in accordance with the programmed prevailing pacing mode. The prevailing pacing mode typically comprises timing out a pacing escape interval that establishes a prevailing pacing rate, delivering a pacing pulse to a heart chamber upon time-out of the pacing escape interval, sensing a characteristic feature of the EGM in the heart chamber during time-out of the pacing escape interval and generating a sense event, and restarting the pacing escape interval upon generation of a sense event. In single chamber atrial pacing systems or bi-atrial pacing systems, the sensed characteristic feature of the EGM that restarts the escape interval is the P-wave. In single chamber ventricular pacing systems or bi-ventricular pacing systems, the sensed characteristic feature of the EGM that restarts the escape interval is the R-wave. In dual chamber pacing modes, e.g., the DDD(R) pacing mode, the pacing escape interval can be characterized as timed between atrial sense events upon detection of P-waves when the spontaneous atrial heart rate exceeds the lower rate limit.

The processing unit 210 is further provided with a memory 315 for storing information related to the patient's spontaneous heart rate as determined and continually updated by the CPU 305 from sensed intrinsic signals, i.e., P-waves and R-waves, as well as pacing data accumulated over a programmable running time interval that is typically seconds, minutes, hours or longer, on a FIFO basis. The spontaneous and stimulated heart rates are calculated on each delivery of a pacing pulse upon time-out of the pacing escape interval or each sense event restating the pacing escape interval and stored over a running time interval. A running count of delivered atrial and/or ventricular pacing pulses and sense events is also maintained over the same or a different time interval. Pacemaker dependency is determined as a percentage (designated P % and more specifically as the atrial P % (A-P %) or the ventricular P % (V-P %) in applicable cases) derived from the ratio of the number of pacing pulses to the total number of pacing pulses and sense events counted over a running time interval preceding the detection of the EMI state. The memory 315 also stores program software for control of or use by the CPU 305 operating in conjunction with hardware and firmware to establish and control the current pacing mode.

The calculation of the MHR and the A-P % and/or V-P % by CPU 305 can occur continually while the pacing system is operating in the prevailing programmed pacing mode or can be conducted only after an interference state is declared, i.e., detected. It would be expected that the augmented interference state pacing rate would be calculated o only after an interference state is declared, but it could be continually calculated as well.

Figure 4:
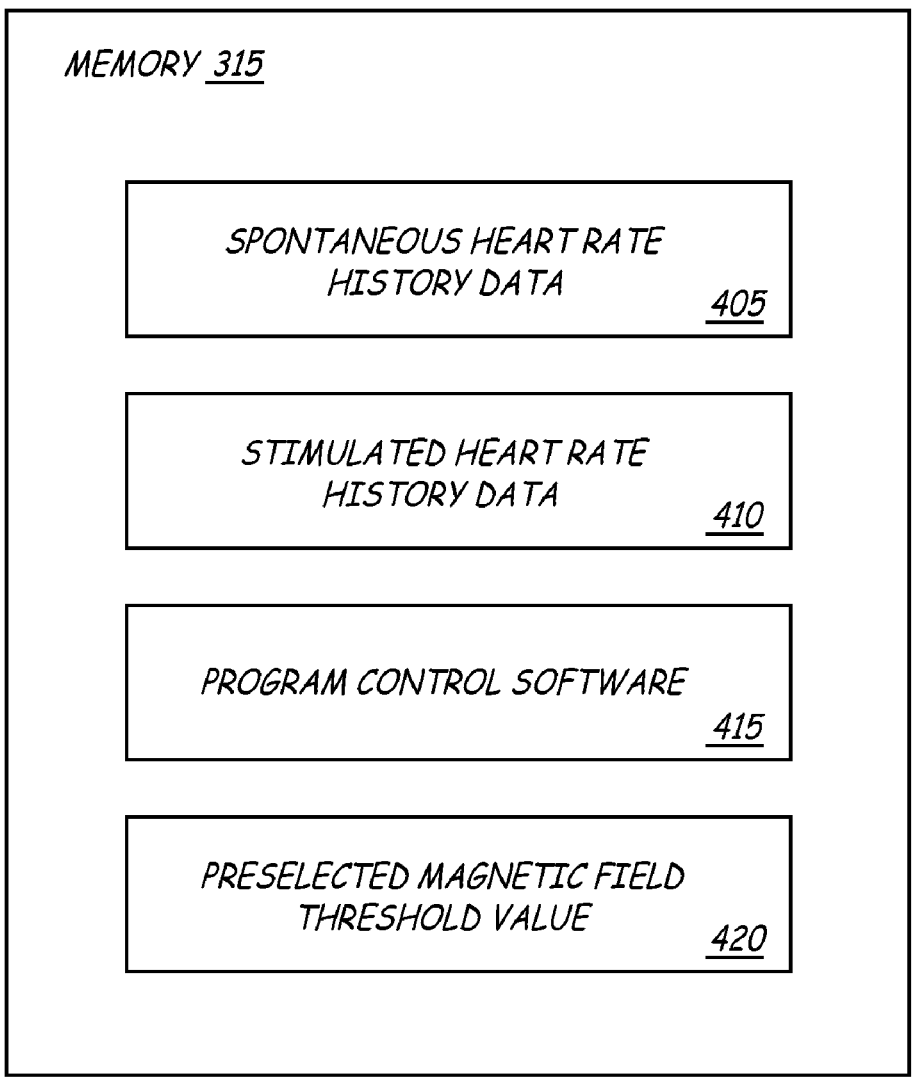
FIG. 4 provides a more detailed representation of a memory of the processor unit of FIG. 3.

A more detailed representation of the memory 315 is shown in FIG. 4 according to the illustrated embodiment. The memory 315 includes a storage area 405 for storing the patient's spontaneous heart rate history data as sensed via the electrodes 117 implanted within the patient's heart 112. A storage area 410 of the memory 315 stores a stimulated heart rate history that indicates the rates at which the IPG 105 paces the atrial and/or ventricular chambers of the patient's heart 112 through the electrodes implanted within the patient's heart. The memory 315 further includes a storage area 415 for storing software to control the processor unit 210 and a storage area 420 for storing pre-selected magnetic field thresholds, which will be described in more detail as this description proceeds. It will be appreciated that the memory 315 may store various other data either in addition to or in lieu of the examples provided above without departing from the spirit and scope of the present invention. Furthermore, it will be appreciated that the data and/or software of the memory 315 may be programmed into or retrieved from their respective storage areas 405–420 utilizing conventional downlink and uplink telemetry transmission techniques via radio frequency (RF) signals, for example.

The IPG 105 may be subjected to low-level magnetic fields during a "magnet test," or in a telemetry session as is conventional in the art referred to herein as a "level 1" magnetic field. When the IPG 105 is exposed to these low level magnetic fields, the IPG 105 enters a magnet mode of operation in which sensing of heart depolarizations is inhibited and pacing pulses are generated at a fixed rate (e.g., 85 bpm) and applied to the patient's heart 112. Usually, the IPG 105 is exposed to these low level magnetic fields during the magnet test for a relatively short period of time (e.g., several seconds). But, the IPG 105 will typically be exposed to a strong magnetic field and high intensity electromagnetic fields for several minutes if not an hour during an MRI scanning session.

The patient's heart rate may increase during the relatively lengthy exposure to the higher-level magnetic field referred to a "level 2" magnetic field to a rate exceeding the magnet mode pacing rate, and the IPG 105 operating in the magnet mode cannot detect this increase of the patient's heart rate and be inhibited by the detected events. Therefore, the dangerous competitive condition of parasystole results if the patient's spontaneous or intrinsic heart rate surpasses the fixed pacing rate during exposure to the higher-level magnetic field. For example, parasystole results if the patient's heart has a spontaneous rate of 95 bpm (beats per minute), and the IPG 105 is attempting to pace the heart at 85 bpm.

Referring again to FIG. 3, the processing unit 210 comprises a magnetic field detector 320 that detects the presence and strength of a magnetic field experienced by the IPG 105. In one embodiment, the magnetic field detector 320 takes the form of a three-dimensional Hall effect magnetic field detector. It will be appreciated, however, that the detector 320 may alternatively take the form of various other magnetic field detectors that detect the presence of a magnetic field and indicate the strength of the field without departing from the spirit and scope of the present invention. In addition, the specific process by which the magnetic field detector 320 detects the presence of a magnetic field and its strength is provided in U.S. patent application Ser. No. 10/059,599 entitled "Method and Apparatus for Detecting Static Magnetic Fields," by Michael B. Terry et al., filed Jan. 29, 2002, and commonly assigned with the present application, the entire contents of which is incorporated herein by reference. Accordingly, the specific techniques employed for magnetic field detection and ascertaining the strength of the detected magnetic field are not disclosed herein to avoid unnecessarily obscuring the present invention.

In accordance with one embodiment of the present invention, a signal indicative of the strength of the magnetic field is sent from the detector 320 to the CPU 305 when the magnetic field detector 320 determines the presence of a magnetic field. In the illustrated embodiment, a first (level 1) pre-selected magnetic field threshold is exceeded, and indicates that the IPG 105 is within the presence of at least a relatively weak magnetic field (such as those produced for the conventional "magnet test") when the magnetic field detector 320 detects the mere presence of a magnetic field. The determination of whether the detected magnetic field exceeds first (level 1) pre-selected magnetic field threshold or a second (level 2) pre-selected magnetic field threshold value can be made employing hardware or software implemented by CPU 305.

In this illustrated embodiment, the CPU 305 determines whether the strength of the detected magnetic field exceeds a second (level 2) pre-selected magnetic field threshold value after the detector 320 detects the presence of the magnetic field (and, thus exceeding a first, (level 1) pre-selected magnetic field threshold stored within the memory 315). In the illustrated embodiment, the second (level 2) pre-selected threshold value is greater than the first (level 1) pre-selected magnetic field threshold and, may be selected so as to indicate the presence of a relatively strong magnetic field that may be produced by an MRI equipment, for example. The second (level 2) pre-selected magnetic field threshold value may be stored within the memory 315 of the processor unit 210 for comparison by the CPU 305 with the strength of the detected magnetic field by the magnetic field detector 320. The storage area 420 (illustrated in FIG. 4) of the memory 315 may store the second (level 2) pre-selected magnetic field threshold value, which may be programmed into memory as previously discussed.

In accordance with the illustrated embodiment, if the strength of the detected magnetic field does not exceed the second (level 2) pre-selected magnetic field threshold, the IPG 105 is disposed in the magnet mode of operation, and the IPG 105 stimulates the patient's heart at a fixed stimulation rate, such as 85 bpm, for example. The magnet mode can be the DOO pacing mode in the case of a dual chamber pacing system normally operating in the DDD(R) pacing mode. The magnet mode can be the AOO or the VOO pacing mode in the case of a single chamber pacing system normally operating in the AAI(R) or the VVI(R) pacing mode, respectively.

The CPU 305 changes the pacing mode to a fixed rate interference state pacing mode if it determines that the strength of the magnetic field detected by the magnetic field detector 320 exceeds the second (level 2) pre-selected magnetic field threshold that is stored in the memory 315. The interference state pacing mode can be the DOO pacing mode in the case of a dual chamber pacing system normally operating in the DDD(R) pacing mode. The interference state pacing mode can be the AOO or the VOO pacing mode in the case of a single chamber pacing system normally operating in the AAI(R) or the VVI(R) pacing mode, respectively. The interference state pacing mode can be other pacing modes as identified in the various embodiments of the invention. Preferably, the CPU 305 only changes the pacing mode to the fixed rate interference state pacing mode if it determines that the strength of the magnetic field detected by the magnetic field detector 320 exceeds the second (level 2) pre-selected magnetic field threshold that is stored in the memory 315.

The CPU 305 also retrieves the spontaneous or stimulated heart rate stored in the memory 315 preceding the detection of the magnetic field by the detector 320. The CPU 305 then increments the stored heart rate by a predetermined increment of that heart rate and utilize the incremented rate as the interference state pacing rate of the IPG 105 for as long as the magnetic field detected by the magnetic field detector 320 exceeds the second (level 2). For example, the predetermined increment may be a ten percent increase of the preceding MHR over a number of paced or spontaneous heart cycles retrieved from the memory 315. Accordingly, if the most recent spontaneous or stimulated heart rate preceding detection of the presence of the magnetic field is 80 bpm, the CPU 305 increments the pacing rate to 88 bpm (i.e., 8 bpm higher or 10% higher than the patient's heart rate prior to the magnetic field being detected). It will be appreciated, however, that the predetermined increment may be a higher or lower percentage of the previously stored spontaneous or stimulated heart rate. It will further be appreciated that the predetermined increment may be a fixed value, such as 10 bpm, for example, that is added to the last stored spontaneous or stimulated heart rate instead of a percentage of the patient's stored spontaneous or stimulated heart rate. Of course, it will be appreciated that the fixed value may be higher or lower than the example provided.

In another embodiment of the present invention, a fixed, maximum pacing rate (possibly corresponding to an upper rate limit), e.g., 120 bpm, may be imposed by the CPU 305. Accordingly, if the last recorded spontaneous or stimulated heart rate of the patient 107 with the addition of the predetermined increment would exceed a pacing rate of 120 bpm, the CPU 305 of the IPG 105 may be configured to maintain a maximum pacing rate of 120 bpm so as not to exceed a stimulated heart rate that may be deemed unsafe to the patient 107. It will be appreciated that the maximum pacing rate set by the IPG 105 may be higher or lower than 120 bpm without departing from the spirit and scope of the present invention. It will further be appreciated that the CPU 305 may further be configured to set a lower or minimum limit on the pacing rate in addition to the maximum pacing rate (discussed above) without departing from the spirit and scope of the present invention. In one embodiment, the maximum and minimum allowable pacing rates may be stored in the memory 315.

In one embodiment of the present invention, the CPU 305 maintains the pacing rate augmented by the predetermined increment (or amount) until the CPU 305 determines that the detected magnetic field by the detector 320 is no longer present. Accordingly, any potential increase in the patient's spontaneous heart rate that cannot be determined during this exposure will likely be lower than the new pacing rate, thus substantially preventing parasystole from occurring.

Figure 5:
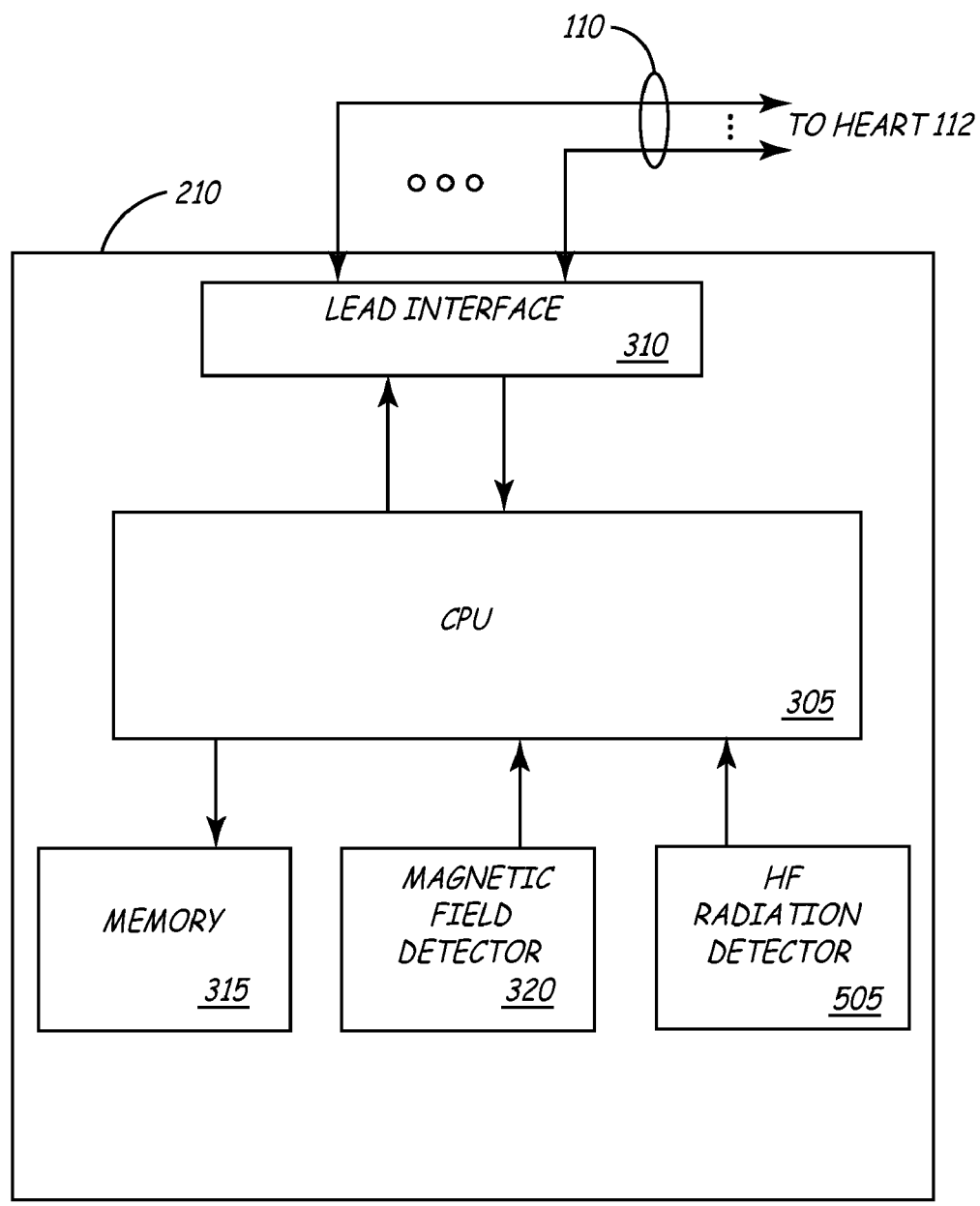
FIG. 5 schematically illustrates a block diagram of the processor unit of FIG. 3 in accordance with another embodiment of the present invention.

The processor unit 210 of the IPG 105 is shown in accordance with an alternative embodiment of the present invention in FIG. 5. In this particular embodiment, the IPG 105 may be alternatively configured to detect the presence of high frequency (HF) radiation interference signals that are produced by radar, high power radio transmitters, and the like. The detection of these HF radiation interference signals may be accomplished via an HF radiation detector 505.

The CPU 305 provides the IPG 105 with an interference state pacing rate corresponding to the MHR increased by the predetermined increment, as previously discussed when the strength of the detected HF radiation interference signals exceeds a pre-selected HF radiation threshold value. The pre-selected HF radiation threshold value may, in one embodiment, be gratis stored in the memory 315 for comparison with the strength of the detected HF radiation interference signals that are detected by the HF radiation detector 505. It will also be appreciated that the HF radiation detector 505 may either be used in lieu of the magnetic field detector 320 or may be used in addition to the magnetic field detector 320 (as depicted in FIG. 5).

Figure 6:
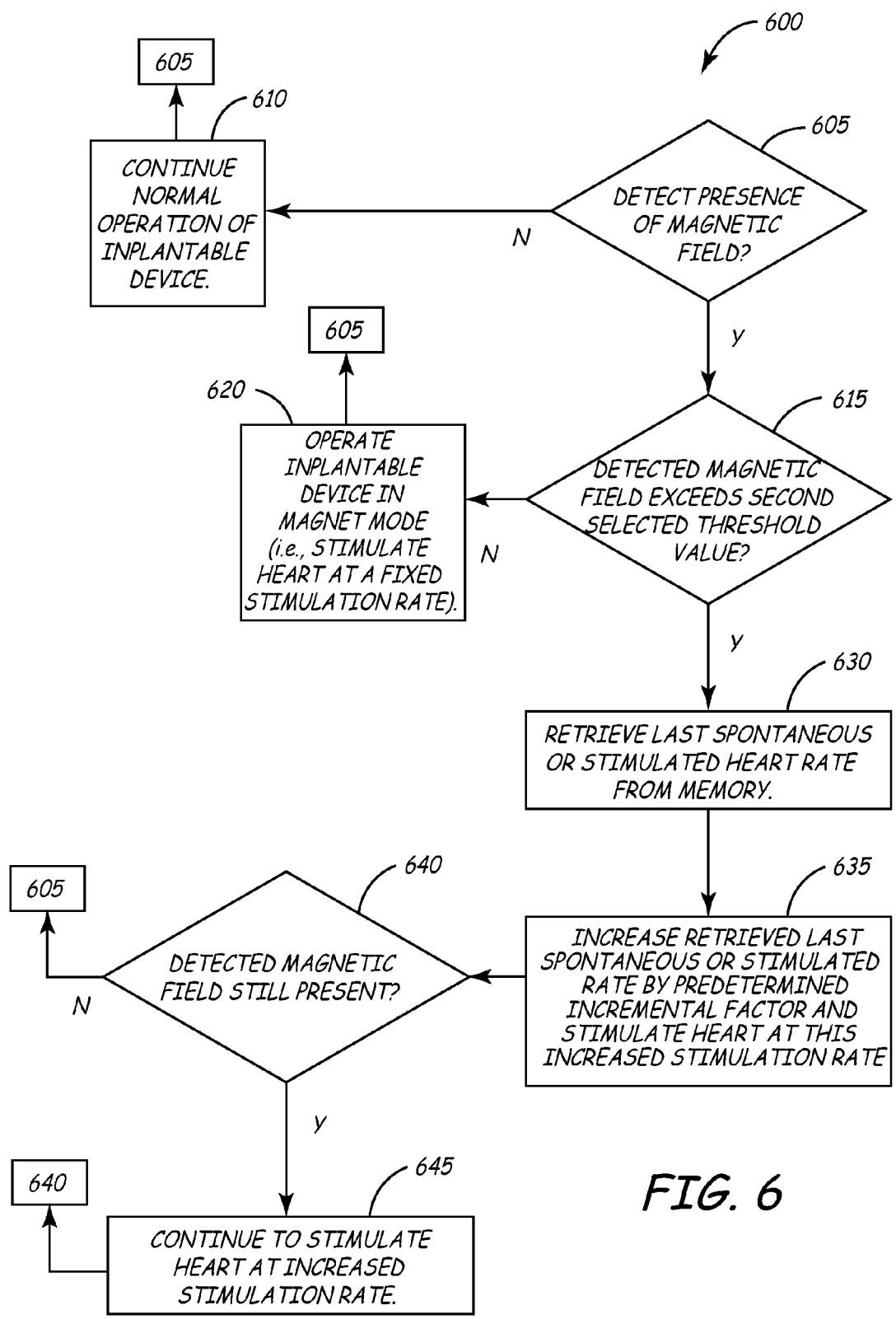
FIG. 6 illustrates a process for controlling the pacing system of FIG. 1 in response to the presence of a strong magnetic field according to one embodiment of the present invention.

Turning now to FIG. 6, a process 600 is illustrated for controlling the IPG 105 in response to the detection of a relatively strong magnetic field, such as those produced by MRI equipment. The process 600 commences in step 605 where the magnetic field detector 320 of the processor unit 120 determines the presence of a magnetic field within the vicinity of the IPG 105. If the magnetic field detector 320 does not determine the presence of a magnetic field in step 605, the IPG 105 continues its normal operation in the prevailing pacing mode in step 610 until the magnetic filed detector 320 detects the presence of a magnetic field in step 605.

If the magnetic field detector 320 detects the presence of a magnetic field in step 605 so as to indicate that a first (level 1) pre-selected magnetic field threshold has been exceeded, the process 600 continues to step 615, where the CPU 305 determines if the strength of the detected magnetic field by the magnetic field detector 320 exceeds a second (level 2) pre-selected magnetic field threshold value. In one embodiment, the second (level 2) pre-selected magnetic field threshold value may be stored in the memory 315 (as shown in FIG. 4) of the processing unit 210 for comparison by the CPU 305 to the strength of the detected magnetic field by the field detector 320. The process 600 proceeds to step 620 where the IPG 105 enters the magnet mode to pace the patient's heart at a fixed pacing rate (e.g., 85 bpm) that is independent of the patient's actual intrinsic rhythm if the strength of the detected magnetic field is lower than the second (level 2) pre-selected magnetic field threshold value stored in the memory 315. The process 600 then reverts back to step 605, where the magnetic field detector 320 determines if the magnetic field is still present.

Alternatively, the process 600 proceeds to step 630 if the magnetic field detected by the detector 320 exceeds the second (level 2) pre-selected magnetic field threshold value as determined in step 615. In step 630, the CPU 305 retrieves the most recent spontaneous or stimulated heart rate (the MHR) stored in the memory 315 prior to satisfaction of step 615. The CPU 305 then augments this retrieved MHR by a predetermined increment in step 635 to derive the interference state pacing rate, and pacing commences in step 635 at the interference state pacing rate. In accordance with the illustrated embodiment, the predetermined increment may be a percentage of the stored spontaneous or stimulated rate, such as 10%, for example. It will further be appreciated that the predetermined increment may be a fixed value of 10 bpm, for example, to be added to the retrieved spontaneous or stimulated MHR to then become the interference state pacing rate of the IPG 105.

The process 600 proceeds to step 640 where it is determined whether the detected magnetic field (level 2) is still present. The interference state is declared over if the detected magnetic field (level 2) is no longer present for a further programmed time duration, e.g. 10 seconds, as determined in step 640. The process 600 reverts back to steps 605 and 610 when the interference state is declared over in step 640. IPG 105 continues to pace the heart 112 at the augmented interference state pacing rate in step 645 if and as long as the detected strong magnetic field (level 2) is determined to be still present in step 640. The further programmed time duration prevents the process 600 from switching back and forth or dithering if the high strength magnetic field fluctuates above and below the level 2 threshold in step 615.

Figure 7:
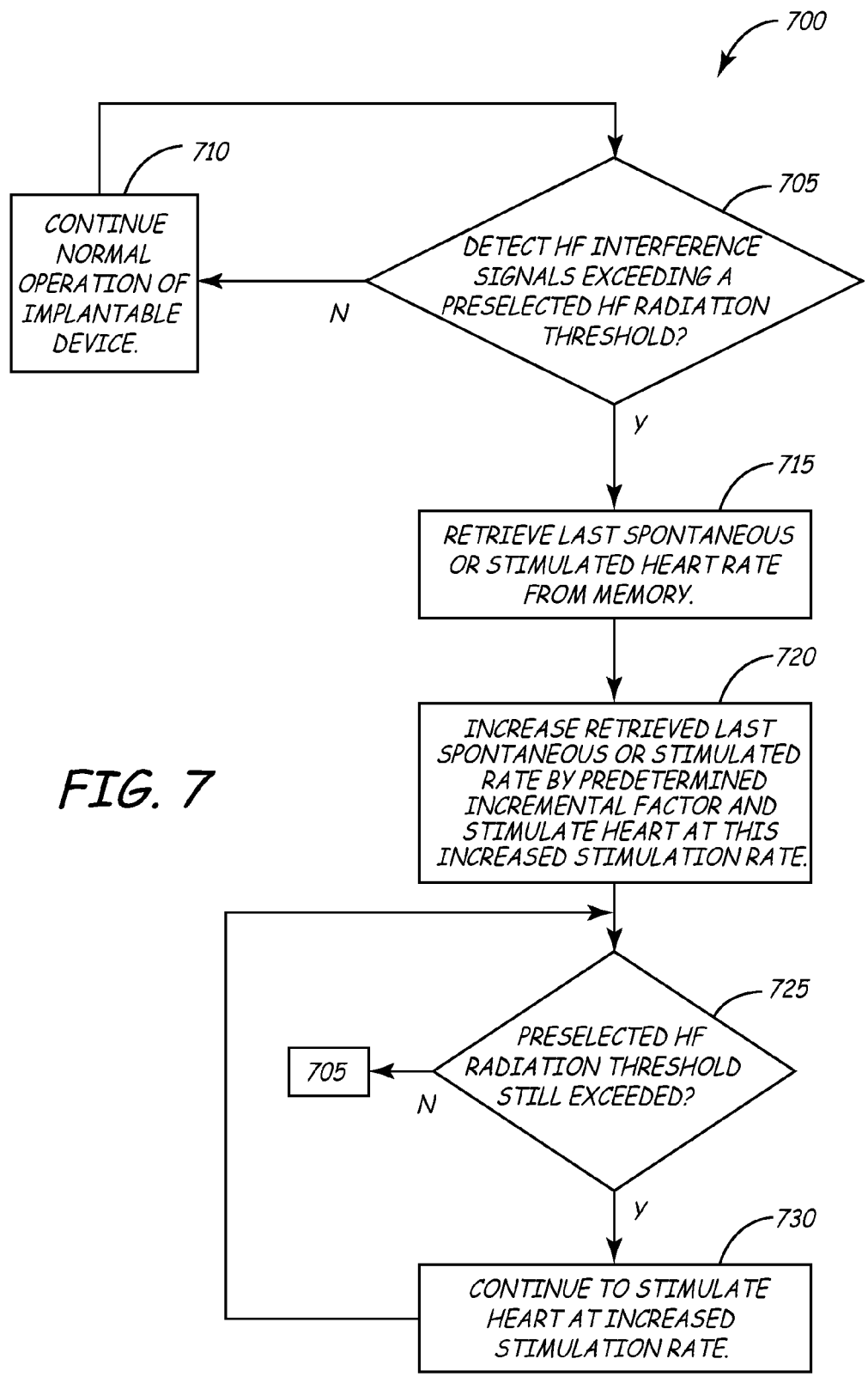
FIG. 7 illustrates a process for controlling the pacing system of FIG. 1 in response to the presence of high frequency radiation interference signals according to another embodiment of the present invention.

Turning now to FIG. 7, a process 700 is illustrated for controlling the pacing mode and rate of IPG 105 in response to the detection of high frequency (HF) radiation interference signals, such as those produced by radar, mobile phone transmitters, and the like. The process 700 commences in decision step 705 where the HF radiation detector 505 of the processor unit 120 determines if any HF radiation interference signals are present that exceed a pre-selected HF radiation threshold. In one embodiment, the pre-selected HF radiation threshold value may be stored in the memory 315 of the processing unit 210 for comparison by the CPU 305 to the strength of the detected HF radiation interference signals by the detector 505.

The process 700 advances to step 710 where the IPG 105 continues operating normally in the programmed pacing mode and at the programmed pacing rate if the strength of the HF radiation interference signals does not exceed the pre-selected HF radiation threshold as determined in step 705.

However, the process 700 proceeds to step 715 if the strength of the detected HF radiation interference signals exceeds the pre-selected HF radiation threshold as determined in step 705. In step 715, the CPU 305 retrieves the most recent spontaneous or stimulated heart rate (the MHR) stored in the memory 315 prior to satisfaction of the pre-selected HF radiation threshold criteria in step 705.

The CPU 305 then augments the retrieved MHR by a predetermined increment in step 720 to derive the interference state pacing rate. Again, in accordance with the illustrated embodiment, the predetermined increment may be a percentage of the stored MHR, such as 10%, for example. It will further be appreciated that the predetermined increment may be a fixed value of 10 bpm, for example, to be added to the last retrieved MHR to become the interference state pacing rate of the IPG 105.

The process 700 proceeds to step 725 where it is determined whether the detected HF radiation interference signals are still present. The interference state is declared over if the detected HF radiation interference signals are no longer present for a further programmed time duration, e.g. 10 seconds, as determined in step 725. The process reverts back to steps 705 and 710 when the interference state is declared over in step 725. IPG 105 paces the heart 112 at the augmented interference state pacing rate in step 730 if and as long as the detected magnetic field is determined to be still present in step 725. The further programmed time duration prevents the process 700 from switching back and forth or dithering if the HF radiation interference signals fluctuate above and below the detection threshold in step 705.

Figure 8:
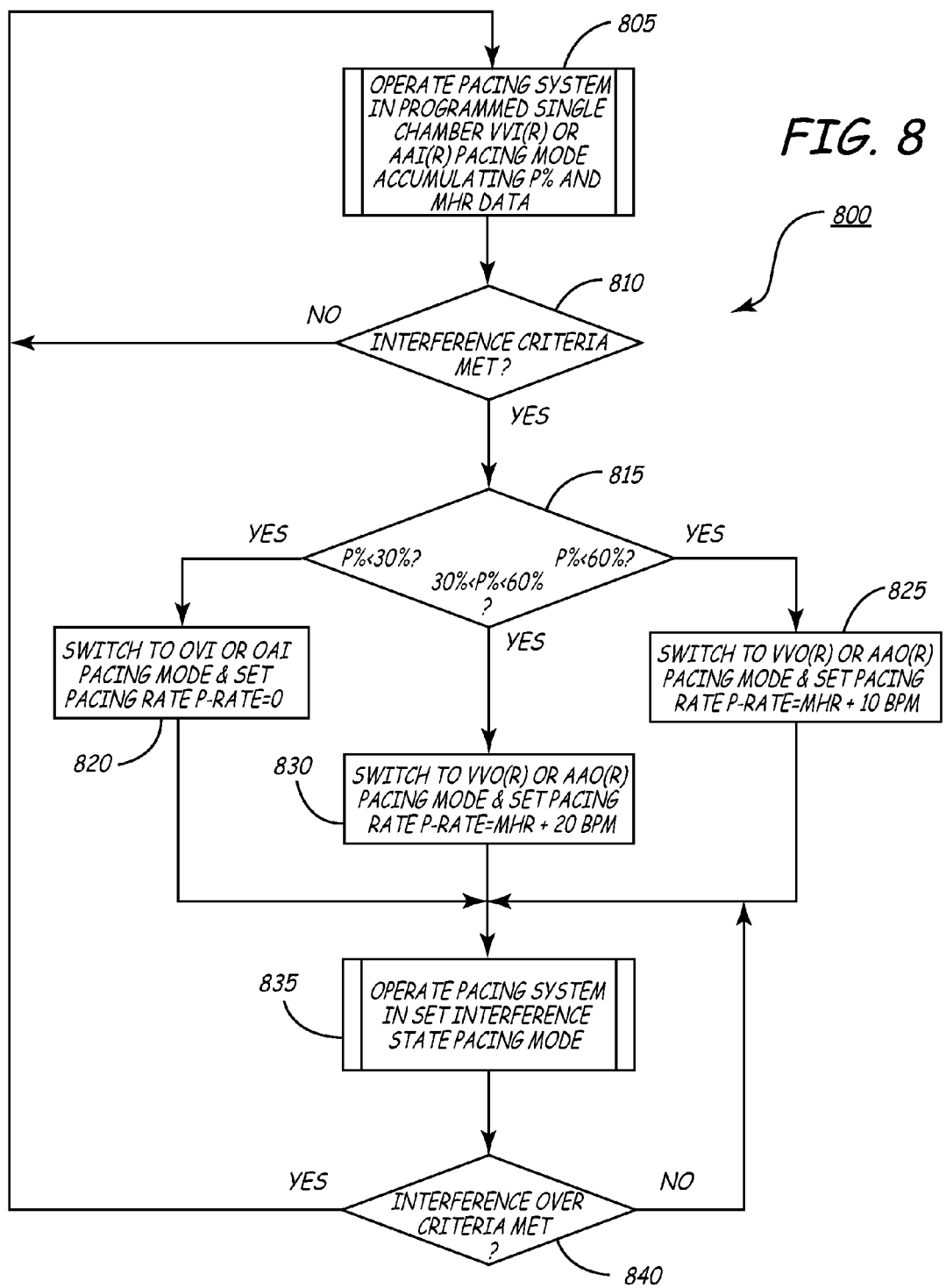
FIG. 8 illustrates a general process for establishing an interference state pacing mode and pacing rate of a pacing system operating in a single chamber pacing mode in response to an interference state caused by the presence of a form of EMI that affects the sense amplifiers ability to accurately generate sense events according to another embodiment of the present invention.
Figure 9A:
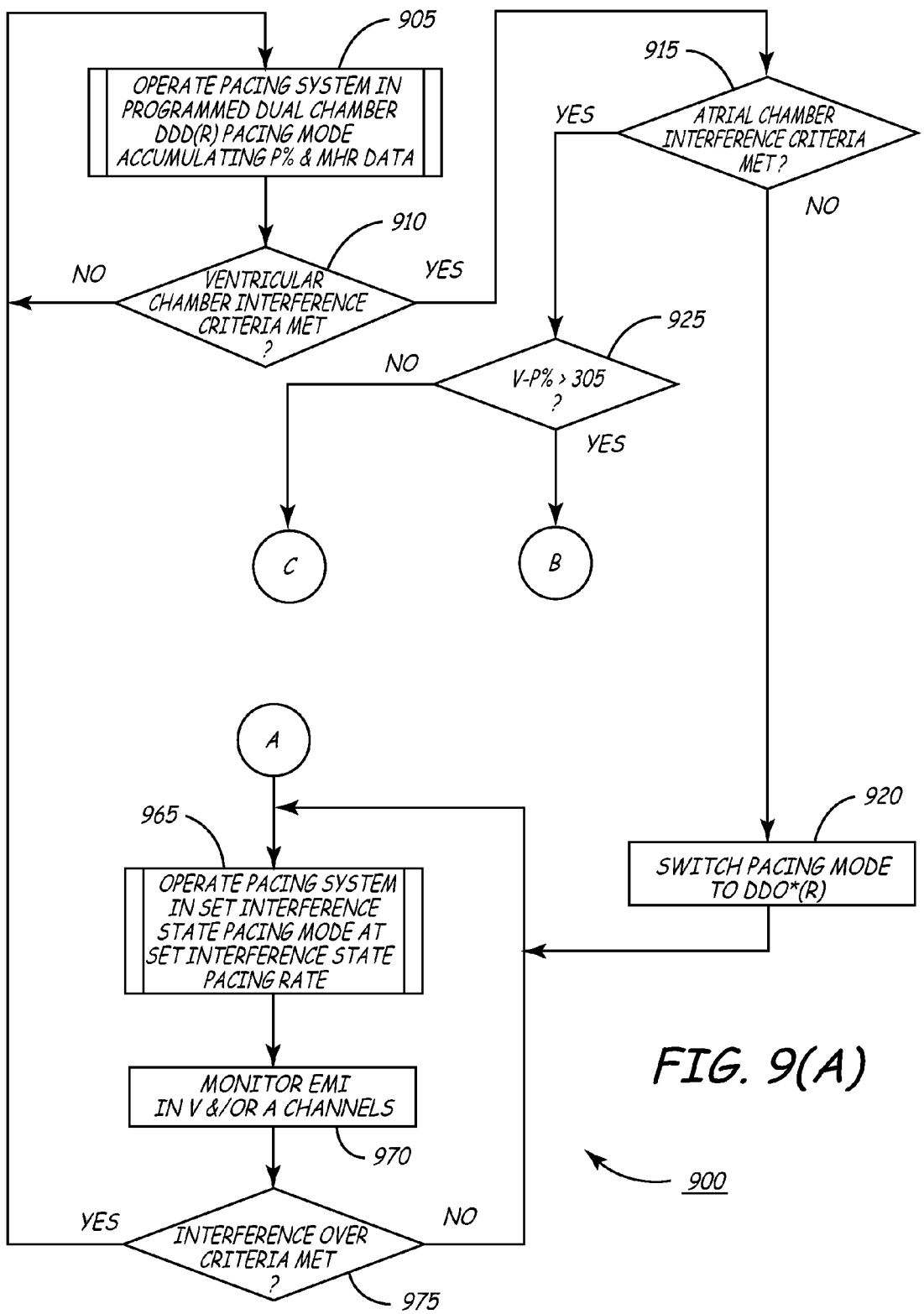
FIGS. 9(a), 9(b), and 9(c) illustrates a process for establishing the interference state pacing mode and rate of a dual chamber pacing system in response to an interference state caused by the presence of a form of EMI that affects the sense amplifiers ability to accurately generate sense events in atrial and/or ventricular sensing channels according to another embodiment of the present invention.
Figure 9B:
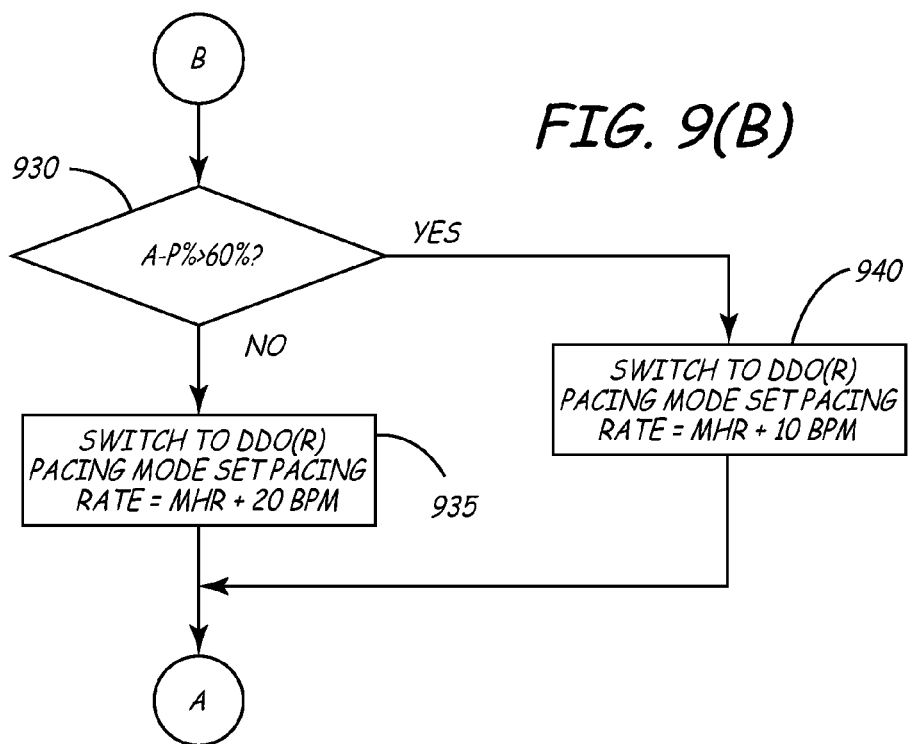
Figure 9C:
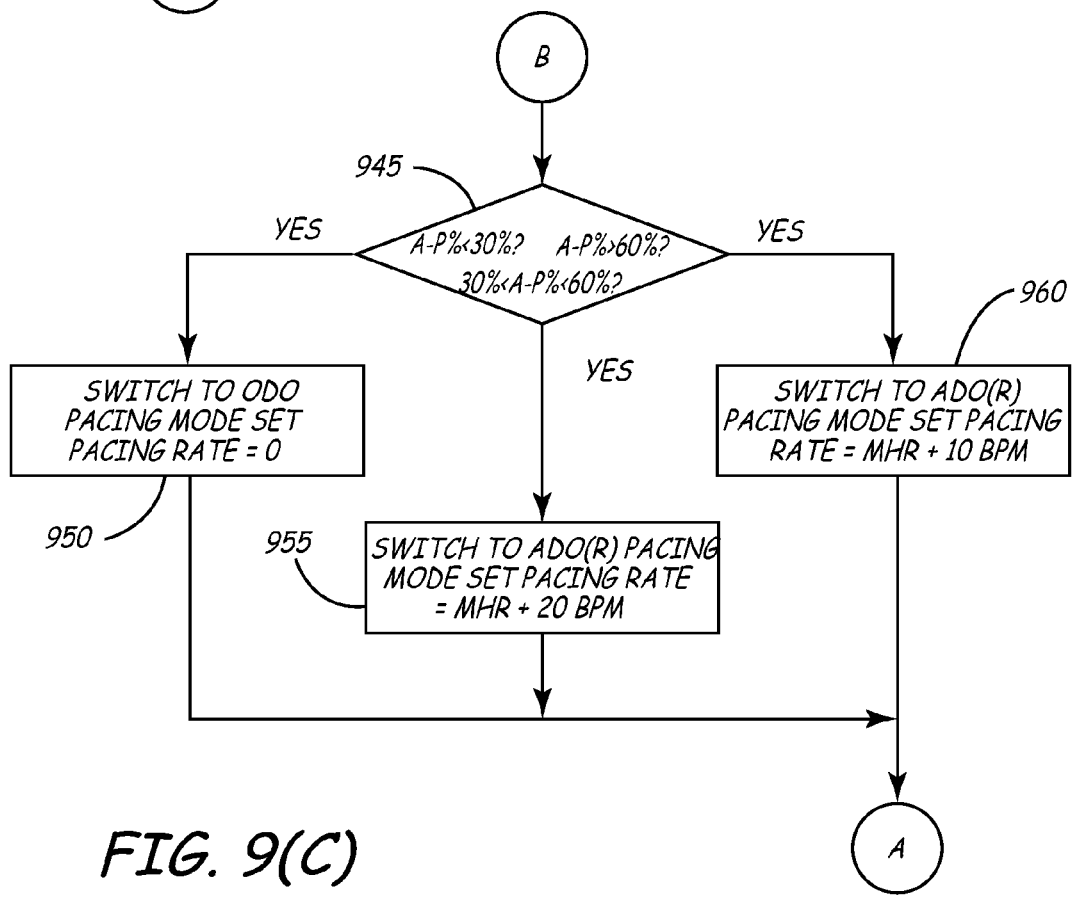
Figure 10:
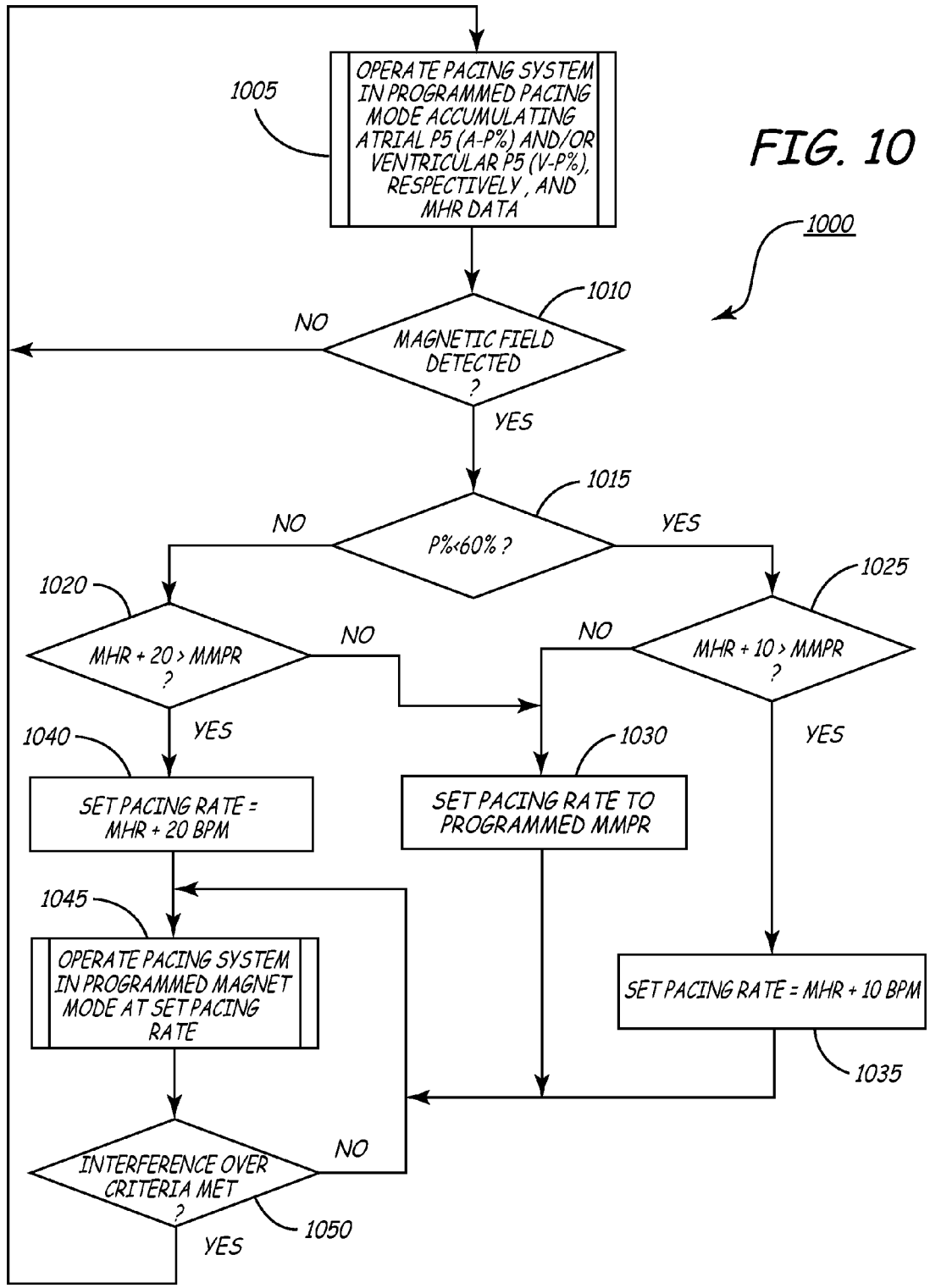
FIG. 10 illustrates a particular process for establishing an interference state pacing mode and pacing rate of a pacing system operating in a single or dual chamber pacing mode in response to an interference state due to the presence of a strong magnetic field according to a further embodiment of the present invention.

In further embodiments of the invention depicted in the flow charts of FIGS. 8–10, the detection of EMI of the above-described types may or may not initiate a change of pacing mode from the prevailing pacing mode to an interference state pacing mode along with establishing an interference state pacing rate that is elevated above the prevailing pacing rate that remains in effect for the duration of the EMI. Returning to FIGS. 4 and 5, CPU 305 accumulates the spontaneous atrial and/or ventricular heart rate history data 405 and the stimulated atrial and/or ventricular heart rate history data 410 over a running time window, e.g., 20 minutes, preceding satisfaction of the EMI detection criteria on a FIFO basis. The CPU 305 calculates an atrial and/or ventricular MHR from the spontaneous atrial and/or ventricular heart rate history data 405 and the stimulated atrial and/or ventricular heart rate history data 410. The CPU 305 also calculates the P % that is an indicator of the degree to which the patient is pacemaker dependent from the spontaneous atrial and/or ventricular heart rate history data 405 and the stimulated atrial and/or ventricular heart rate history data 410 during the window. The MHR and the P % determined by CPU 305 from the data 405 and 410 accumulated in a FIFO manner in registers of memory 315 are also maintained in a continually updated register of the memory 315 as described with reference to FIG. 4. The MHR and P % data is employed to establish an interference state pacing mode and pacing rate of the atria and/or ventricles in dual or single chamber pacing systems. In these embodiments, the augmented interference state pacing rate is derived by summing the MHR with a programmed fixed increment, e.g., 10 bpm or 20 bpm. It will be understood that the augmented interference state pacing rate can be alternatively derived by summing the MHR with a calculated percentage of the MHR in the manner illustrated in the above-described embodiments.

FIG. 8 illustrates a process 800 for establishing the pacing rate of the pacing system 100 of FIG. 1 operating in atrial or ventricular single chamber pacing modes, in response to the presence of forms of EMI that corrupt the atrial or ventricular EGM or otherwise affecting the atrial and ventricular sense amplifiers ability to accurately detect atrial and ventricular features of the EGM that are of interest as described above according to another embodiment of the present invention. This may or may not occur during exposure to high strength magnetic fields as during MRI scanning. It is anticipated that noise detection algorithms performed by the CPU 305 or embodied in firmware are implemented that would cause the pacing system to enter a conventional reversion pacing mode. The particular interference state pacing modes and interference state pacing rates provided by the process 800 depend upon the degree of pacemaker dependency of the patient's heart and the MHR.

The pacing system is operating in the programmed single chamber pacing mode and accumulating MHR data in step 805. The programmed pacing mode would typically be the VVI(R) or the AAI(R) pacing mode, that is pacing modes inclusive of the VVI and AAI pacing modes at a programmed pacing rate and rate responsive VVIR and AAIR pacing modes. In a VVIR or AAIR pacing mode, the prevailing pacing rate determined by a pacing escape interval is adjusted in step 805 between a pacing lower rate, e.g. 60 bpm, and a pacing upper rate limit, e.g., 120 bpm, as a function of the physiologic need for cardiac output as determined by a sensor derived RCP according to any of the rate response modes known in the art.

Pacing is provided in step 805 in the prevailing pacing mode and pacing rate until the interference criteria are met and an interference state is declared in step 810. In particular, an interference state is declared in step 810 whenever one of the EMI detection criteria is met in either steps 615 and 715 or other EMI detection criteria are met that would cause the pacing system to normally enter the reversion mode. Interference criteria can be defined in any of the ways described above in step s 605 and 705 as well as in other ways known in the art.

When the interference state is declared in step 810, the interference state pacing mode and pacing rate are set in steps 820 or 825 or 830 for the duration of the interference state determined in steps 835 and 840 depending upon the prevailing pacing mode and pacing rate and the degree to which the patient is pacemaker dependent upon onset of the interference state. The applicable atrial P % (A-P %) or ventricular P % (V-P %) is compared to fixed or programmable pacemaker dependency thresholds comprising a programmable pacemaker independency threshold, e.g., 30%, a programmable pacemaker dependency threshold, e.g., 60%. Pacing can be inhibited or set to a particular interference state rate dependent upon the results of the comparison made in decision step 815 (which represents a series of three decision steps).

If the prevailing P % is less than 30% (P %<30%), the patient is declared pacemaker independent in decision step 815. Then, the pacing mode switches from the prevailing VVI(R) or AAI(R) mode to an inhibited mode OVI or OAI, respectively, in step 820, and pacing system operates in that mode in step 835 on the assumption that the patient's intrinsic heart rate will suffice to provide adequate cardiac output for the duration of the interference state. Thus, the interference pacing rate (P-Rate) is set to 0 bpm (P-Rate=0) in this case.

If the prevailing P % is greater than 60% (P %>60%), the patient is declared pacemaker dependent in decision step 815. Then, the pacing mode switches from the prevailing VVI(R) or AAI(R) mode to a fixed rate mode VVO(R) or AAO(R), respectively, in step 825. The interference pacing rate is made dependent upon the MHR in step 825 by incrementing the MHR by a first rate increment that may be fixed or programmable or may depend upon the MHR. In the illustrated embodiment, the interference pacing rate P-Rate=MHR+10 bpm on the assumption that the patient's intrinsic heart rate should be overdriven slightly to ensure adequate cardiac output for the duration of the interference state and to avoid parasystole.

The prevailing P % can fall between the pacemaker independency threshold and the pacemaker dependency threshold (30%<P %<60%). In that case, the patient is declared moderately pacemaker dependent, and the pacing mode switches from the prevailing VVI(R) or AAI(R) pacing mode to the respective VVO(R) or AAO(R) pacing mode VVO or AAO, respectively, in step 830. The interference pacing rate is made dependent upon the MHR in step 830 by incrementing the MHR by a second rate increment that may be fixed or programmable or may depend upon the MHR. In the illustrated embodiment, the interference pacing rate P-Rate=MHR+20 bpm on the assumption that the patient's intrinsic heart rate should be overdriven more aggressively to ensure adequate cardiac output for the duration of the interference state and to avoid parasystole.

Pacing in the interference state mode and at the interference state rate determined in step 820, 825 or 830 continues in step 835 until the interference criteria are no longer met as determined in decision step 840. The "interference over" criteria employed in step 840 can be the same or different than the detection criteria employed in decision step 810.

The VVO(R) and AAO(R) pacing modes and the VVO and AAO pacing modes are not typical programmed pacing modes. These pacing modes enable the respective ventricular and atrial sense amplifiers so that spontaneous depolarizations can be sensed to the extent that they might occur and it is possible to do so in the presence of EMI but the pacing escape interval is not restarted upon any generated sense events. Thus, the enabled sense amplifiers make it possible to determine whether the EMI that caused the interference criteria to be met continues in decision step 840. EMI influenced heart rate data can also be accumulated along with a date and time tag identifying the episode, the duration of the episode, the interference state modes entered, and the calculated interference state pacing rate and stored in memory for uplink telemetry analysis at a later date for diagnostic purposes.

A dual chamber process 900 is shown in FIGS. 9(*a*), 9(*b*), and 9(*c*) for establishing the interference state pacing mode and pacing rate of a pacemaker or pacing system operating in a dual chamber DDD(R) pacing mode in step 905 when interference criteria are detected in steps 910 and 915. The EMI in this case is also limited to electrical interference from any source that distorts or corrupts the atrial and/or ventricular EGM signals being sensed by the respective atrial and ventricular sense amplifiers in such ways that the EMI is declared present by EMI detection algorithms in one or both of the atrial and ventricular sensing channels.

Very generally speaking, the pacing system operates in a prevailing programmed dual chamber pacing mode in step 905, e.g., the DDD(R) pacing mode. Such dual chamber pacing systems have an atrial sensing channel including an atrial sense amplifier that generates an atrial sense event upon detection of a predetermined characteristic of the atrial EGM, a ventricular sensing channel including a ventricular sense amplifier that generates a ventricular sense event upon detection of a predetermined characteristic of the ventricular EGM, an atrial pacing pulse generator for delivering atrial pacing pulses to at least one atrial heart chamber, means for timing an AV delay from an atrial sense event or a delivered atrial pacing pulse, and inhibiting means for stopping the time-out of the AV delay if a ventricular sense event is generated during time-out of the AV delay, and a ventricular pacing pulse generator for delivering ventricular pacing pulses to at least one ventricular heart chamber upon time-out of the AV delay. Non-refractory atrial sense events occurring at a rate exceeding the pacing lower rate and up to an upper rate limit reset the time-out of the pacing escape interval and commence the time-out of the AV delay to trigger delivery of a ventricular pacing pulse at its time-out. Non-refractory ventricular sense events occurring during the AV delay effectively stop the time-out of the AV delay and thereby inhibit the delivery of a ventricular pacing pulse at the time-out of the AV delay. An A-A escape interval can be defined comprising the AV delay and a V-A interval, and non-refractory ventricular sense events during the V-A delay can cause the restarting of the V-A delay depending on the timing of the ventricular event. In the DDDR pacing mode, the A-A pacing escape interval is adjusted in step 905 between the pacing lower rate, e.g. 60 bpm, and the pacing upper rate limit, e.g., 120 bpm, as a function of the physiologic need for cardiac output in any of the rate response modes known in the art.

The CPU 305 calculates the MHR and the atrial P % or A-P % that is an indicator of the degree to which the patient is pacemaker dependent in the atria from the spontaneous atrial heart rate history data 405 and the stimulated atrial heart rate history data 410. The CPU 305 also calculates the ventricular P % or V-P % that is an indicator of the degree to which the patient is pacemaker dependent in the ventricles from the spontaneous ventricular heart rate history data 405 and the stimulated ventricular heart rate history data 410.

In this embodiment, ventricular sense events are compared to interference detection criteria in step 910 established in any of the ways known in the art of noise detection to declare a ventricular interference state. If a ventricular interference state is declared in step 910, then atrial sense events are compared to interference detection criteria in step 915 established in any of the ways known in the art of noise detection to confirm or not confirm the declaration of the ventricular interference state. If the declared ventricular interference state cannot be confirmed by examination of the atrial sense events in step 915 with respect to the atrial interference criteria, then the pacing mode is switched in step 920 to a particular form of dual chamber pacing that we characterize for convenience herein as the "DDO*(R)" interference state pacing mode. In this particular variation of dual chamber pacing, atrial and ventricular synchronous pacing continues at the prevailing pacing rate established by atrial sense events and the rate control parameter that adjusts the escape interval. Atrial sense events and delivered atrial pacing pulses start an AV delay, and a ventricular pacing pulse is delivered at time-out of the AV delay regardless of whether a ventricular sense event is generated during time-out of the AV delay when EMI is only found affecting the ventricular sensing channel. In this way, the inhibiting means is prevented from stopping the time-out of the AV upon generation of a ventricular sense event when electromagnetic interference is determined to be present in the ventricular sensing channel and is not determined to be present in the atrial sensing channel.

In this DDO*(R) interference state pacing mode, the atria and ventricles can be synchronously paced when the A-A escape interval, established either as the lower rate limit or varying as a function of a RCP between the lower rate limit and the upper rate limit, times out, or the ventricles can be paced synchronously with each nonrefractory atrial sense event spontaneously occurring between the lower rate limit and the upper rate limit.

The DDO*(R) interference state pacing mode is carried out in step 965 while EMI is monitored in step 970. This DDO*(R) interference state pacing mode enables the atrial and ventricular sense amplifiers to continue to sense spontaneous depolarizations and noise to the extent that they might occur and it is possible to do so but the pacing escape interval is not restarted upon any generated sense events. Thus, it is possible to continue to monitor EMI in both the atrial and ventricular sensing channels in step 970 to determine whether the EMI that caused the interference criteria to be met continues in decision step 975. EMI influenced heart rate data can also be accumulated along with a date and time tag identifying the episode, the duration of the episode, the interference state modes entered, and the calculated interference state pacing rate and stored in memory for uplink telemetry analysis at a later date for diagnostic purposes.

But, if the declaration of ventricular interference is confirmed in step 915, then the V-P % is compared to a ventricular pacemaker independency threshold, e.g. 30% in this example, in decision step 925. The interference state pacing mode and pacing rate is set by steps 930–940 shown in FIG. 9(b) if the patient is determined in step 925 to be pacemaker dependent in the ventricles to the extent that V-P %>30%. The interference state pacing rate is set by steps 945–960 shown in FIG. 9(c) if the patient is determined in step 925 to be pacemaker independent in the ventricles as determined.

In FIG. 9(b), the A-P % is compared to the fixed or programmable pacemaker dependency thresholds comprising an atrial pacemaker dependency threshold, e.g., 60%, in decision step 930. If the prevailing A-P % is greater than 60% (A-P %>60%), the patient is declared pacemaker dependent in decision step 940. In step 940, the pacing mode is switched from the prevailing DDD(R) pacing mode to the classic DDO(R) pacing mode where atrial and ventricular pacing is not inhibited or triggered by a atrial and ventricular sense events, and the interference state pacing rate is set to MHR+10 bpm. If the prevailing A-P % is not greater than 60% (A-P %<60%), the patient is declared somewhat pacemaker independent in decision step 935. In step 935, the pacing mode is switched from the prevailing DDD(R) pacing mode to the classic DDO(R) pacing mode, and the interference state pacing rate is set to MHR+20 bpm. The 10 bpm and 20 bpm increments can either be fixed or made programmable. The interference state pacing rate P-Rate=MHR+20 bpm is established in step 935 on the assumption that the patient's intrinsic heart rate is more likely to increase and should be overdriven more aggressively to avoid parasystole. The interference state pacing rate is augmented by 10 bpm (P-Rate=MHR+10 bpm) in step 945 on the assumption that the patient's intrinsic heart rate need not be overdriven as aggressively for the duration of the interference state to avoid parasystole.

The DDO(R) interference state pacing mode is carried out in step 965 while EMI is monitored in step 970. This atypical pacing mode enables the atrial and ventricular sense amplifiers to continue to sense spontaneous depolarizations and noise to the extent that they might occur and it is possible to do so but the pacing escape interval is not restarted upon any generated sense events. Thus, it is possible to continue to monitor EMI in both the atrial and ventricular sensing channels in step 970 to determine whether the EMI that caused the interference criteria to be met continues in decision step 975. EMI influenced heart rate data can also be accumulated along with a date and time tag identifying the episode, the duration of the episode, the interference state modes entered, and the calculated interference state pacing rate and stored in memory for uplink telemetry analysis at a later date for diagnostic purposes.

In FIG. 9(c), the A-P % is compared to an atrial pacing independency threshold, e.g., 30%, and an atrial pacing dependency threshold, e.g., 60% in decision step 945 (which represents a series of three decision steps). If the prevailing A-P % is less than 30% (A-P %<30%), the patient is declared pacemaker independent in decision step 945, and the pacing mode switches from the prevailing DDD(R) pacing mode to an inhibited mode ODO in step 950. Atrial and ventricular pacing and sensing are inhibited in the interference state mode ODO in step 950 on the assumption that the patient's intrinsic heart rate will suffice to provide adequate cardiac output for the duration of the interference state. Thus, the interference state pacing rate (P-Rate) is set to 0 bpm (P-Rate=0) and any sensing is inhibited in this case.

The ODO "pacing mode" is an atypical pacing mode that inhibits any pacing but enables the atrial and ventricular sense amplifiers to continue to sense spontaneous depolarizations and noise to the extent that they might occur and it is possible to do so but the pacing escape interval is not restarted upon any generated sense events. Thus, it is possible to continue to monitor EMI in both the atrial and ventricular sensing channels in step 970 to determine whether the EMI that caused the interference criteria to be met continues in decision step 975. EMI influenced heart rate data can also be accumulated along with a date and time tag identifying the episode, the duration of the episode, the interference state modes entered, and the calculated interference state pacing rate and stored in memory for uplink telemetry analysis at a later date for diagnostic purposes.

The prevailing A-P % can fall between the pacemaker independency threshold and the pacemaker dependency threshold (30%<A-P %<60%). If that condition is satisfied in step 945, the pacing mode is switched in step 955 from the prevailing DDD(R) pacing mode to the ADO(R) interference state pacing mode providing only atrial pacing and sensing. The atrial interference pacing rate P-Rate is made dependent upon the MHR in step 955 by incrementing the MHR by a first rate increment that may be fixed or programmable or may depend upon the MHR. In the illustrated embodiment, the interference state pacing rate is augmented in step 955 by 20 bpm (P-Rate=MHR+20 bpm) on the assumption that the patient's intrinsic heart rate should be overdriven more aggressively for the duration of the interference state to avoid parasystole.

The prevailing A-P % can exceed the pacemaker dependency threshold A-P %>60%. If that condition is satisfied in step 945, the pacing mode is switched in step 960 from the prevailing DDD(R) pacing mode to the ADO(R) interference state pacing mode providing only atrial pacing and sensing. The interference state pacing rate P-Rate is made dependent upon the MHR in step 960 by incrementing the MHR by a second rate increment that may be fixed or programmable or may depend upon the MHR. In the illustrated embodiment, the interference state pacing rate is augmented in step 960 by 10 bpm (P-Rate=MHR+10 bpm) on the assumption that the patient's intrinsic heart rate need not be overdriven as aggressively for the duration of the interference state to avoid parasystole.

Again, the ADO(R) pacing mode is an atypical pacing mode that inhibits any pacing in the ventricles but enables the atrial and ventricular sense amplifiers to continue to sense spontaneous depolarizations and noise to the extent that they might occur and it is possible to do so but the pacing escape interval is not restarted upon any generated sense events. Thus, it is possible to continue to monitor EMI in both the atrial and ventricular sensing channels in step 970 to determine whether the EMI that caused the interference criteria to be met continues in decision step 975. EMI influenced heart rate data can also be accumulated along with a date and time tag identifying the episode, the duration of the episode, the interference state modes entered, and the calculated interference state pacing rate and stored in memory for uplink telemetry analysis at a later date for diagnostic purposes.

Returning to FIG. 9(a), pacing in the interference state pacing mode and at the interference state pacing rate determined in steps 920 or 930–940 or 945–960 continues in step 965 until the interference criteria are no longer met as determined in decision step 975. The EMI continues to be monitored in steps by the ventricular and/or atrial sensing channels in step 970 as described above. The "interference over" criteria employed in step 975 can be the same or different than the detection criteria employed in decision steps 910 and 915.

FIG. 10 illustrates a process 1000 of a particular embodiment of the invention wherein the response of a single or dual chamber pacing system having a magnet mode response to a detected magnetic field is modified to take into account the MHR and the degree to which the patient is pacemaker dependent. As described above, the magnet mode of pacing systems is customarily a fixed rate pacing mode, e.g., DOO, VOO or AOO, at a fixed rate, e.g., 85 bpm, that prevails when exposed to such low strength and high strength magnetic fields. The process 1000 accounts for and prevent parasystole that could take place when the heart spontaneously contracts during fixed rate pacing occurring in the typical magnet mode. The process 1000 can be implemented to be operable upon detection of a high strength magnetic field (level 2), e.g., during MRI scanning as described above, or to be operable when a low strength magnetic field (level 1) is detected during a diagnostic procedure or a telemetry session or during exposure to the high strength magnetic field (level 2).

The process 1000 operates when such a magnetic field exceeding a programmed magnetic field threshold is detected in step 1010 in the manner described above with respect to the magnetic field detector 320 of FIGS. 3 and 5. The fixed rate magnet mode, e.g., DDO, VDO or ADO, is entered, but the fixed pacing rate is set to the programmed magnet mode pacing rate under certain conditions related to the determination that the patient is pacemaker dependent and the relationship of the magnet mode pacing rate to the MHR. The interference state pacing rate is set to programmed magnet mode pacing rate or to the sum of the MHR and an increment depending upon the relation of the sum of the MHR and the increment to the magnet mode pacing rate and the degree to which the patient is pacemaker dependent.

In step 1005, the pacing system operates in the programmed single chamber or dual chamber pacing mode accumulating the atrial P % (A-P %) and/or ventricular P % (V-P %) and MHR data as described above. In step 1005, the cardiac pacing system operates in a prevailing pacing mode comprising timing out a pacing escape interval that establishes a prevailing pacing rate, delivering a pacing pulse to a heart chamber upon time-out of the pacing escape interval, sensing a characteristic feature of the EGM in the heart chamber during time-out of the pacing escape interval and generating a sense event, and restarting the pacing escape interval upon generation of a sense event. Furthermore, data is accumulated from the sense events and delivered pacing pulses over a predetermined time interval to derive the MHR and the pacing dependency percentage P % representing the ratio of delivered pacing pulses to the sum of delivered pacing pulses and sensed events over the predetermined time interval in step 1005.

An interference state is declared when a magnetic field is detected exceeding the programmed threshold in step 1010, and the patient is determined to be pacemaker dependent or pacemaker independent in step 1015 by comparing the pacing dependency percentage P % to a pacemaker dependency threshold, e.g. 60%. The patient is declared pacemaker dependent if P %>60% or pacemaker independent if P %<60%.

The magnet mode pacing rate (MMPR) is compared to the sum of the mean heart rate and a first rate increment, e.g. 10 bpm in step 1025 if the patient is determined to be pacemaker independent in step 1015. In step 1035, the pacing escape interval is set to establish an interference state pacing rate equal to the sum of the MHR and the first rate increment if the sum of the MHR and the first rate increment exceeds the MMPR as determined in step 1025. In step 1030, the pacing escape interval is set to establish the MMPR if the sum of the MHR and the first rate increment does not exceed the MMPR as determined in step 1025.

The MMPR is compared to the sum of the mean heart rate and a second rate increment greater than the first rate increment, e.g. 20 bpm in step 1020 if the patient is determined to be pacemaker dependent in step 1015. In step 1040, the pacing escape interval is set to establish an interference state pacing rate equal to the sum of the MHR and the first rate increment if the sum of the MHR and the second rate increment exceeds the MMPR as determined in step 1020. Again, in step 1030, the pacing escape interval is set to establish the MMPR if the sum of the MHR and the second rate increment does not exceed the MMPR as determined in step 1020.

Then, the pacing system is operated in step 1045 in the ADO, VDO or DDO magnet mode employing the magnet mode pacing rates set in one of steps 1030, 1035 and 1040 until the interference criteria are no longer met as determined in decision step 1050. The "interference over" detection criteria employed in step 1050 is likely to be the same but could be different than the detection criteria employed in decision step 1010.

The above described embodiments of the invention and equivalents thereto may advantageously be embodied in single chamber and/or dual chamber pacing systems that typically deliver pacing to right heart chamber(s) as well as in multi-chamber pacing systems that deliver pacing to right and left, upper and/or lower, heart chambers and in multi-site pacing systems that deliver pacing to multiple sites of one or more heart chamber.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. A method of operating a pacing system to respond to a presence of electromagnetic interference tending to corrupt the features of an electrogram, comprising:

accumulating data from sense events and delivered pacing pulses over a predetermined time interval, deriving a mean heart rate from the accumulated data, and deriving a pacing dependency percentage representing the ratio of delivered pacing pulses to the sum of delivered pacing pulses and sensed events over the predetermined time interval;

declaring an interference state if electromagnetic interference tending to corrupt the features of the electrogram is detected;

determining whether the patient is pacemaker dependent or pacemaker independent from the pacing dependency percentage;

during the declared interference state:

setting a pacing mode of the pacing system to an inhibited pacing mode if the patient is determined to be pacemaker independent, whereby pacing pulses are not delivered to the heart chamber;

setting the pacing mode to a fixed rate pacing mode if the patient is determined to be pacemaker dependent, whereby a pacing escape interval is not restarted by a sense event and pacing pulses are delivered to the heart chamber at a fixed rate; and adjusting the pacing escape interval to provide an interference state pacing rate exceeding the mean heart rate by a predetermined increment; and operating the pacing system in the interference state pacing mode at the interference state pacing rate, whereby the patient's heart is paced while minimizing occurrences of parasystole.

2. The method of claim 1, wherein the step of determining if the patient is pacemaker dependent or pacemaker independent comprises:

establishing a pacing dependency threshold;

comparing the pacing dependency percentage to the pacing dependency threshold;

declaring the patient pacemaker dependent when the pacing dependency percentage exceeds the pacing dependency threshold; and declaring the patient pacemaker independent when the pacing dependency percentage falls below the pacing dependency threshold.

3. The method of claim 1, wherein:

the step of determining if the patient is pacemaker dependent or pacemaker independent comprises:

establishing a first pacing dependency threshold and a second pacing dependency threshold exceeding the first pacing dependency threshold;

comparing the pacing dependency percentage to the first and second pacing dependency thresholds;

declaring the patient pacemaker independent when the pacing dependency percentage falls below the first pacing dependency threshold;

declaring the patient pacemaker dependent when the pacing dependency percentage exceeds the second pacing dependency threshold; and declaring the patient moderately pacemaker dependent when the pacing dependency percentage falls between the first and second pacing dependency thresholds; and the adjusting step comprises:

adjusting the pacing escape interval to provide a first interference state pacing rate exceeding the mean heart rate by a first predetermined increment when the patient is declared pacemaker dependent, whereby the patient's heart is paced while minimizing occurrences of parasystole; and adjusting the pacing escape interval to provide a second interference state pacing rate exceeding the mean heart rate by a second predetermined increment greater than the first predetermined increment when the patient is declared moderately pacemaker dependent, whereby the patient's heart is paced while minimizing occurrences of parasystole.

4. A system that operates a pacing system to respond to a presence of electromagnetic interference tending to corrupt the features of an electrogram, comprising:

means for accumulating data from sense events and delivered pacing pulses over a predetermined time interval, for deriving a mean heart rate from the accumulated data, and for deriving a pacing dependency percentage representing the ratio of delivered pacing pulses to the sum of delivered pacing pulses and sensed events over the predetermined time interval;

means for declaring an interference state upon detecting electromagnetic interference tending to corrupt the features of the electrogram;

means for determining whether the patient is pacemaker dependent or pacemaker independent from the pacing dependency percentage;

means for setting a pacing mode of the pacing system to an inhibited pacing mode if the patient is determined to be pacemaker independent, whereby pacing pulses are not delivered to the heart chamber;

means for setting the pacing mode to a fixed rate pacing mode if the patient is determined to be pacemaker dependent, whereby the pacing escape interval is not restarted by a sense event and pacing pulses are delivered to the heart chamber at a fixed rate; and means for adjusting a pacing escape interval to provide an interference state pacing rate exceeding the mean heart rate by a predetermined increment, whereby the patient's heart is paced while minimizing occurrences of parasystole.

5. The system of claim 4, wherein the means for determining if the patient is pacemaker dependent or pacemaker independent comprises:

means for establishing a pacing dependency threshold;

means for comparing the pacing dependency percentage to the pacing dependency threshold;

means for declaring the patient pacemaker dependent when the pacing dependency percentage exceeds the pacing dependency threshold; and means for declaring the patient pacemaker independent when the pacing dependency percentage falls below the pacing dependency threshold.

6. The system of claim 4, wherein:

the means for determining if the patient is pacemaker dependent or pacemaker independent comprises:

means for establishing a first pacing dependency threshold and a second pacing dependency threshold exceeding the first pacing dependency threshold;

means for comparing the pacing dependency percentage to the first and second pacing dependency thresholds;

means for declaring the patient pacemaker independent when the pacing dependency percentage falls below the first pacing dependency threshold;

means for declaring the patient pacemaker dependent when the pacing dependency percentage exceeds the second pacing dependency threshold; and means for declaring the patient moderately pacemaker dependent when the pacing dependency percentage falls between the first and second pacing dependency thresholds; and the adjusting means comprises:

means for adjusting the pacing escape interval to provide a first interference state pacing rate exceeding the mean heart rate by a first predetermined increment when the patient is declared pacemaker dependent, whereby the patient's heart is paced while minimizing occurrences of parasystole; and means for adjusting the pacing escape interval to provide a second interference state pacing rate exceeding the mean heart rate by a second predetermined increment greater than the first predetermined increment when the patient is declared moderately pacemaker dependent, whereby the patient's heart is paced while minimizing occurrences of parasystole.

* * * * *

UNITED STATES PATENT AND TRADEMARK OFFICE
CERTIFICATE OF CORRECTION

PATENT NO. : 7,082,328 B2  
APPLICATION NO. : 10/143392  
DATED : July 25, 2006  
INVENTOR(S) : Hermann D. Funke Page 1 of 1

It is certified that error appears in the above-identified patent and that said Letters Patent is hereby corrected as shown below:

On the Title Page

Item (12):  
"Funke" should read -- Funke et al. --

Item (75) Inventor, please add the following Inventors:  
Giorgio Corbucci, Cento (IT), Massimo Ceccarelli, Cesena (IT)

Signed and Sealed this  
Twenty-second Day of December, 2020

Andrei Iancu  
*Director of the United States Patent and Trademark Office*